(12) United States Patent
Geng et al.

(10) Patent No.: US 11,464,794 B2
(45) Date of Patent: *Oct. 11, 2022

(54) COMPOSITION OF ALGINIC OLIGOSACCHARIC DIACIDS

(71) Applicants: GREEN VALLEY (SHANGHAI) PHARMACEUTICALS CO., LTD., Shanghai (CN); SHANGHAI INSTITUTE OF MATERIA MEDICA, CHINESE ACADEMY OF SCIENCES, Shanghai (CN)

(72) Inventors: Meiyu Geng, Shanghai (CN); Zhenqing Zhang, Shanghai (CN); Yingshen Jin, Shanghai (CN); Zhongping Xiao, Shanghai (CN); Jian Ding, Shanghai (CN)

(73) Assignees: GREEN VALLEY (SHANGHAI) PHARMACEUTICALS CO., LTD., Shanghai (CN); SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/256,853

(22) PCT Filed: Jun. 28, 2019

(86) PCT No.: PCT/CN2019/093778
§ 371 (c)(1),
(2) Date: Dec. 29, 2020

(87) PCT Pub. No.: WO2020/001632
PCT Pub. Date: Jan. 2, 2020

(65) Prior Publication Data
US 2021/0260085 A1    Aug. 26, 2021

(30) Foreign Application Priority Data

Jun. 29, 2018    (CN) .......................... 201810721327.6

(51) Int. Cl.
*A61K 31/702* (2006.01)
*A61P 25/28* (2006.01)
*A61P 29/00* (2006.01)

(52) U.S. Cl.
CPC .......... *A61K 31/702* (2013.01); *A61P 25/28* (2018.01); *A61P 29/00* (2018.01)

(58) Field of Classification Search
None
See application file for complete search history.

(56) References Cited

U.S. PATENT DOCUMENTS

| 8,835,403 | B2 * | 9/2014 | Geng | ........................ A61P 5/50 |
| | | | | 514/53 |
| 2020/0385417 | A1 * | 12/2020 | Geng | ................. A61K 31/7032 |

FOREIGN PATENT DOCUMENTS

| CN | 100508985 C | 7/2009 |
| CN | 106344592 A | 1/2017 |
| CN | 106344593 A | 1/2017 |
| CN | 106344594 A | 1/2017 |
| CN | 106344595 A | 1/2017 |
| WO | 2016188382 A1 | 12/2016 |

OTHER PUBLICATIONS

Yang, Z., Li, J. P., & Guan, H. S. (2004). Preparation and characterization of oligomannuronates from alginate degraded by hydrogen peroxide. Carbohydrate polymers, 58(2), 115-121. (Year: 2004).*
Jiang, R. W., Du, X. G., Zhang, X., Wang, X., Hu, D. Y., Meng, T., . . . & Shen, J. K. (2013). Synthesis and bioassay of β-(1,4)-D-mannans as potential agents against Alzheimer's disease. Acta Pharmacologica Sinica, 34(12), 1585-1591. (Year: 2013).*
Athari Nik Azm, S., Vafa, M., Sharifzadeh, M., Safa, M., Barati, A., & Mirshafiey, A. (2017). Effects of M2000 (D-mannuronic acid) on learning, memory retrieval, and associated determinants in a rat model of Alzheimer's disease. American Journal of Alzheimer's Disease & Other Dementias®, 32(1), 12-21. (Year: 2017).*
International Search Report and Written Opinion for Application No. PCT/CN2019/093778, dated Oct. 8, 2019, 11 pages.
European Office Action for Application No. 19825647.1, dated Mar. 14, 2022, 11 pages.

* cited by examiner

*Primary Examiner* — Dale R Miller
(74) *Attorney, Agent, or Firm* — McCarter & English, LLP; Wei Song; Sudheer Chava

(57) ABSTRACT

The present invention relates to an alginic oligosaccharic diacid composition comprising a mannuronic diacid of Formula (IV) or a pharmaceutically acceptable salt thereof, wherein n is an integer selected from 1 to 9, m is selected from 0, 1 or 2, m' is selected from 0 or 1, and wherein the total weight of alginic oligosaccharic diacid wherein n=1-5 accounts for more than 60% of the total weight of the composition; the total weight of guluronic acids accounts for less than 50% of the total weight of the composition.

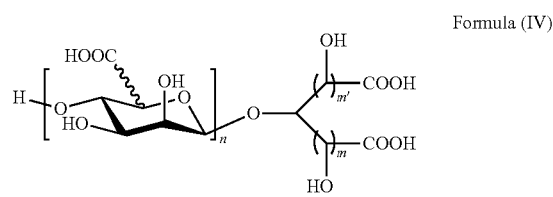

Formula (IV)

17 Claims, 16 Drawing Sheets

The reaction above can be simplified as follows:

COMPOSITION OF ALGINIC OLIGOSACCHARIC DIACIDS

CROSS-REFERENCE TO RELATED APPLICATIONS

This application is a U.S. national stage filing, under 35 U.S.C. § 371(c), of International Application No. PCT/CN2019/093778, filed on Jun. 28, 2019, which claims priority to Chinese Patent Application No. 201810721327.6, filed on Jun. 29, 2018.

TECHNICAL FIELD

The present invention relates to an optimal composition of alginic oligosaccharic diacids obtained by a biological activity screening method, which uses an Alzheimer's disease animal model to evaluate the effects of different polymerization degrees of alginic oligosaccharides and proportions thereof on biological activity. Finally, a composition with the best biological activity is obtained from screening and a desired target substance is prepared by the method of ultrafiltration membrane separation

BACKGROUND OF THE INVENTION

Alginic oligosaccharides have been paid extensive attention due to their potential medicinal values. Alginic oligosaccharides are usually prepared by multiple steps with alginic acid as a raw material.

In the alginic oligosaccharide molecules of the raw material, there is an M segment formed of D-mannuronic acids linked by β-1,4-glucosidic bonds, a G segment formed of L-guluronic acids linked by α-1,4-glucosidic bonds, and an MG segment formed by hybridization of the two saccharides. The structural formulae of D-mannuronic acid and L-guluronic acid are shown in Formula (I) and Formula (II) below:

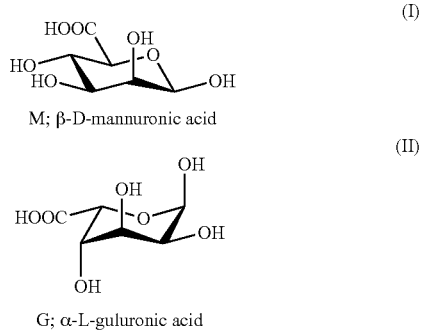

The structural formula of alginic oligosaccharides is shown by Formula (III) below:

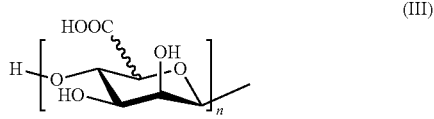

The M segment and the G segment can be separated from the raw material, alginic acids. A common method can be simply described below: alginic acid is preliminarily degraded to give mixed polysaccharides of polymannuronic acid and polyguluronic acid; then the mixed polysaccharides are subjected to acidic precipitation to remove a certain amount of polyguluronic acid therein. See, e.g., the methods disclosed in Chinese Patent Application No. 98806637.8 and CN02823707.2.

A method for preparing oligomeric mannuronic acid is as follows: the M-segment intermediate obtained above can be subjected to further acidolysis by heating under an acidic condition to obtain a small fragment mannuronic acid polymer having a desired molecular weight range. In addition, the degradation efficiency can be improved by an oxidative degradation method; meanwhile, the reducing end can be oxidized to a ring-opened saccharic diacid, see Chinese Patent Application No. 200580009396.5 (Patent literature 1) filed by Meiyu Geng, et al. and U.S. Pat. No. 8,835,403 B2 (Patent literature 2) for details. For convenience of description, Patent literatures 1 and 2 are hereinafter collectively referred to as prior documents, which are incorporated herein by reference in their entirety.

The reaction to obtain mannuronic diacid disclosed in prior documents can be represented by FIG. 23, that is, the aldehyde group at position C1 of mannuronic acid at the reducing end of oligomannuronic acid polysaccharide is oxidized to carboxyl group.

In the above oxidative conversion process, a commonly used oxidant is an alkaline copper sulfate solution, i.e. Fehling's reagent. Prior documents adopt this oxidation method. Specifically, under an alkaline condition, the reaction substrate polymannuronic acid, i.e. the above M-segment intermediate, is added to a copper sulfate solution and reacted in a boiling water bath for 15 minutes to 2 hours. This method uses Cu' ion as an oxidant to oxidize the aldehyde group, and a brick-red cuprous oxide precipitate is generated in the reaction. This reaction is often used to identify a reducing sugar.

Prior documents disclose that oligomannaric acids have effects against Alzheimer's disease (AD) and Diabetes Mellitus, and the activity of oligomannaric acids with a polymerization degree of 6 is the best. The pathogenesis of Alzheimer's disease and type 2 diabetes is closely related to amyloids (β-amyloid and amylin). Amyloid protein aggregates and then produces protein oligomers, which further aggregate to form fibers. These protein aggregates are cytotoxic, induces an oxidative reaction in cells to damage mitochondria, and triggers a cascade reaction such as inflammatory reaction, causing damages to a large number of neurons and β cells, and ultimately leading to onset of Alzheimer's disease and type 2 diabetes. Oligomannaric acids target amyloid protein and antagonize the cascade reactions induced by the amyloid protein, and therefore have the effects of preventing and treating Alzheimer's disease and type 2 diabetes.

In order to obtain the oligomannaric acid having the anti-Alzheimer's disease and anti-diabetic effects disclosed in the prior documents, the guluronic acid in the raw material alginic acid needs to be removed. The content of the guluronic acid in the alginic acid is usually above 30%, maximally up to about 70%. Thus, in order to obtain high-purity oligomannaric acid, the actual production cost is very high.

SUMMARY OF THE INVENTION

The first aspect of the present invention relates to an alginic oligosaccharic diacid composition comprising a mannuronic acid of Formula (IV) and/or guluronic acid or a pharmaceutically acceptable salt thereof:

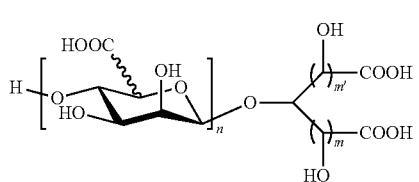

Formula (IV)

wherein n is an integer selected from 1 to 9, m is selected from 0, 1 or 2, m' is selected from 0 or 1, and wherein, the total weight of alginic oligosaccharic diacids wherein n=1-5 accounts for more than 60% of the total weight of the composition; the total weight of guluronic diacids accounts for less than 50% of the total weight of the composition.

Another aspect of the present invention relates to a pharmaceutical composition or health care product, which comprises the above-mentioned alginic oligosaccharic acid composition. Other aspects of the present invention also relate to the application of the composition of alginic oligosaccharic acid in the treatment of diseases selected from Alzheimer's disease, Parkinson's disease, inflammation, pain, Diabetes Mellitus or vascular dementia.

In particular, the alginic oligosaccharic acid composition of the present invention is a mixture of mannuronic acid and guluronic acid with different polymerization degrees, and its main components are oligosaccharide with a polymerization degree of 2 to 10: an M segment formed of mannuronic acids linked by β-1,4-glucosidic bonds, a G segment formed of guluronic acids linked by α-1,4-glucosidic bonds, and an MG segment formed by hybridization of the two saccharides. It is known that mannuronic diacids have certain pharmacological activities against Alzheimer's disease (AD) and Diabetes Mellitus. The most active saccharides are pentasaccharide to octasaccharide, especially hexasaccharide. However, the inventors find that the oligosaccharic diacid mixture of mannuronic acid and guluronic acid with a polymerization degree of 2 to 10 also has pharmacological activities against Alzheimer's disease (AD) and Diabetes Mellitus, but the premise is that the content of guluronic acid is controlled within a certain range. In other words, the alginic oligosaccharic diacid composition of the present invention can be prepared with greatly reduced production cost, which makes it easier to realize in actual production and easy to realize industrialized mass production.

DETAILED DESCRIPTION OF THE INVENTION

Figure 1:
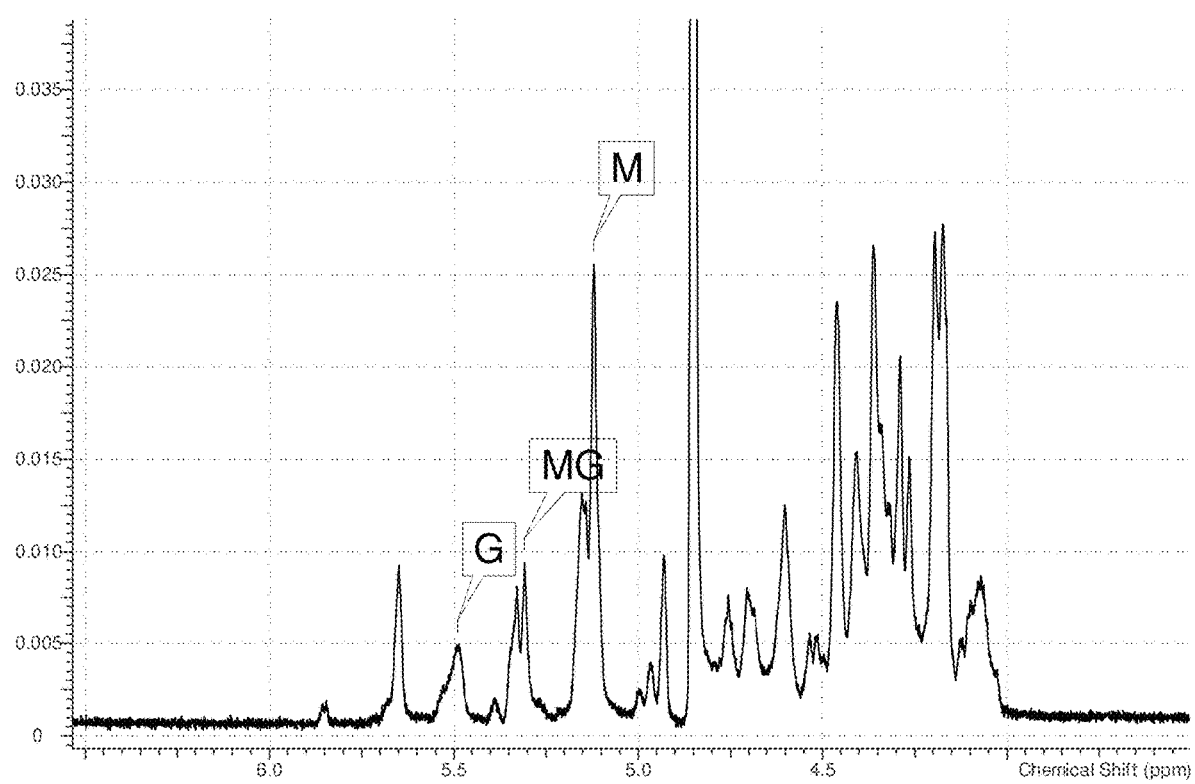
FIG. 1 shows NMR spectrum of intermediate.

Various aspects of the present invention will be described in detail below, but the present invention is not limited to these specific embodiments. Those skilled in the art can make some modifications and adjustments to the present invention according to the substantial disclosure below, and these adjustments are also within the scope of the present invention.

Alginic Oligosaccharic Diacid Composition

The first aspect of the present invention relates to an alginic oligosaccharic diacid composition comprising mannuronic acid of Formula (IV) and/or guluronic acid or a pharmaceutically acceptable salt thereof:

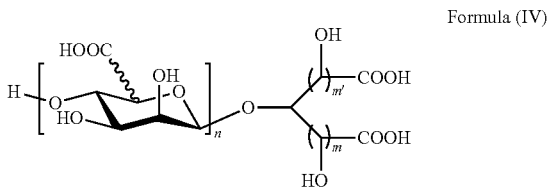

Formula (IV)

wherein n is an integer selected from 1 to 9, m is selected from 0, 1 or 2, m' is selected from 0 or 1, and wherein, the total weight of the alginic oligosaccharic diacid wherein n=1-5 accounts for more than 60% of the total weight of the composition;

wherein, the total weight of guluronic diacids accounts for less than 50% of the total weight of the composition.

The alginic oligosaccharic acid composition of the present invention is a mixture of mannuronic acid and guluronic acid with different polymerization degrees, and its main components are oligosaccharide with a polymerization degree of 2 to 10: an M segment formed of mannuronic acids linked by β-1,4-glucosidic bonds, a G segment formed of guluronic acids linked by α-1,4-glucosidic bonds, and an MG segment formed by hybridization of the two saccharides. According to the prior applications, it is known that mannuronic diacids have pharmacological activities against Alzheimer's disease (AD) and Diabetes Mellitus, wherein the most active saccharides in mannuronic diacids are pentasaccharide to octasaccharide, especially hexasaccharide. However, different from the known prior art, the inventors find that the oligosaccharic diacid mixture of mannuronic acid and guluronic acid with a polymerization degree of 2 to 10 also has pharmacological activities against Alzheimer's disease (AD) and Diabetes Mellitus, but the content of guluronic acid needs to be controlled within a certain range.

In the actual preparation process, the content of guluronic acid in the product after the preliminary degradation of the original alginic acid as described above is usually over 30%, and maximally up to about 70%. If following the prior applications, in order to obtain the oligomannaric acid with high activity, the guluronic acid must be removed through separation as much as possible. However, based on the above discovery of the inventors, it is not required to separate and remove guluronic acid from the degraded product. Further, the inventors find that by controlling the proportion of guluronic acid within a certain range through the control of the conditions of the acid precipitation reaction, the activity of the obtained composition can reach or even be better than that of the oligomannaric acid hexasaccharide disclosed in the prior applications. Also, since guluronic acid does not need to be removed as an impurity, the product yield is significantly higher than the product yield disclosed in the prior applications. Thus, it greatly reduces the production cost, reduces the waste discharge, thereby being easier to realize in the actual production, and being easier to realize industrial large-scale production.

According to a preferred embodiment, in the alginic oligosaccharic diacid composition of the present invention, the total weight of alginic oligosaccharic diacids wherein n=1-5 accounts for 80-95% of the total weight of the composition and the total weight of guluronic acids accounts for less than 50% of the total weight of the composition.

According to a preferred embodiment, in the alginic oligosaccharic diacid composition of the present invention, the ratio of the total weight of alginic oligosaccharic diacids with low polymerization degree wherein n=1-3 to the total weight of alginic oligosaccharic diacids with low polymerization degree wherein n=4-7 is between 1.0 and 3.5.

According to a preferred embodiment, in the alginic oligosaccharic diacid oligosaccharide composition of the present invention, the total weight of alginic oligosaccharic diacids wherein m+m'=1 or 2 is no less than 50% of the total weight of the composition, preferably 60%-90%, more preferably 70%-90%. In particular, in the alginic oligosaccharic diacid composition, the total weight of alginic oligosaccharic diacids wherein m+m'=1 is no less than 10% of the total weight of the composition, preferably 30-40%. In another preferred embodiment, in the alginic oligosaccharic diacid composition, the total weight of alginic oligosaccharic diacids wherein m+m'=2 is no less than 10% of the total weight of the composition, preferably 30-50%.

According to a preferred embodiment, in the alginic oligosaccharic diacid composition of the present invention, the total weight of alginic oligosaccharic diacids wherein n=1-5 accounts for 80-95% of the total weight of the composition.

According to a preferred embodiment, in the alginic oligosaccharic diacid composition of the present invention, the total weight of alginic oligosaccharic diacids wherein n=1-3 accounts for 20-70% of the total weight of the composition.

According to a preferred embodiment, in the alginic oligosaccharic diacid composition of the present invention, the ratio of the total weight of alginic oligosaccharic diacids wherein n=1-3 to the total weight of alginic oligosaccharic diacids wherein n=4-7 is between 1.0 and 3.5, preferably between 1.0 and 3.0.

According to a preferred embodiment, in the alginic oligosaccharic diacid composition of the present invention, the weight percentage content of the alginic oligosaccharic diacids with each of polymerization degrees in the above composition is: disaccharide 5-25%, trisaccharide 15-30%, tetrasaccharide 15-28%, pentasaccharide 10-25%, hexasaccharide 5-15%, heptsaccharide 3-10%, octasaccharide 2-5%, nonasaccharide 1-5%, decasaccharide 1-5%. In particular, in the composition, the weight percentage content of oligosaccharides in the above composition is: disaccharide 10-20%, trisaccharide 18-30%, tetrasaccharide 15-28%, pentasaccharide 15-20%, hexasaccharide 5-15%, heptsaccharide 3-5%, octasaccharide 2-3%, nonasaccharide 1-3%, decasaccharide 1-3%.

According to a preferred embodiment, in the alginic oligosaccharic diacid composition of the present invention, the total weight of aguluronic acids wherein n=1-3 accounts for 0.1-50% of the total weight of the composition, preferably 1-30%.

In the alginic oligosaccharic diacid composition of the present invention, the pharmaceutically acceptable salt thereof is sodium salt or potassium salt.

Method for Preparing the Alginic Oligosaccharic Diacid Composition

Process for preparing the alginic oligosaccharic diacid of the present invention is summarized as follows:

After preliminary degradation of alginic acid, a mixed polysaccharide of polymannuronic acid and polyguluronic acid can be obtained. The mixed polysaccharide is then precipitated by acidic method to remove a certain amount of polyguluronic acid. In the process of the precipitation by the acidic method, the higher the pH, the higher the polyguluronic acid content in the obtained mixed polysaccharide is. See, e.g., the methods disclosed in Chinese Patent Application No. 98806637.8 and CN02823707.2. In the presence of an oxidant, the sugar chains of the aforementioned mixed polysaccharide undergo oxidative degradation to obtain oxidized oligosaccharides with different polymerization degrees. The oxidized oligosaccharides are characterized by the oxidation of the mannuronic acid or the guluronic acid at the reducing end of the oligosaccharide to saccharic diacid with 3-6 carbons.

The oxidant that is particularly advantageous for the reaction of the present invention is ozone. During the reaction process, the oxidative degradation reaction of sugar chains can occur when ozone is introduced into the solution containing mixed polysaccharides. The temperature at which the oxidative degradation step is carried out is preferably 0-70° C., more preferably 10-45° C. The pH value of the above oxidative degradation step is 3-13, preferably 4-10, more preferably 6-8.

The oxidative degradation reaction using ozone in the present invention, acidic hydrolysis in the presence of the alkaline copper sulfate (prior document) or hydrogen peroxide and sodium hypochlorite (Chinese Patent Application 01107952.5) used in the prior art are common in that the three methods can degrade the sugar chains. The difference is that the reducing end structure of the sugar chain of the degradation product is different. The reducing end of the oxidative degradation product, mannuronic acid or guluronic acid, obtained in the present invention comprises a diacid structure with 3-6 carbons. In addition, the process used in the oxidative degradation step of the present invention has other advantages: 1. the reaction conditions are mild and no special reaction conditions are required; 2. the ozone used can be prepared at the reaction site, reducing the pressure of transportation in industrial production; 3. after the reaction, ozone is automatically decomposed into oxygen without the hazard of residual reagents, which will not cause environmental pollution, either. The reaction process is shown in FIG. 24.

Figure 24:
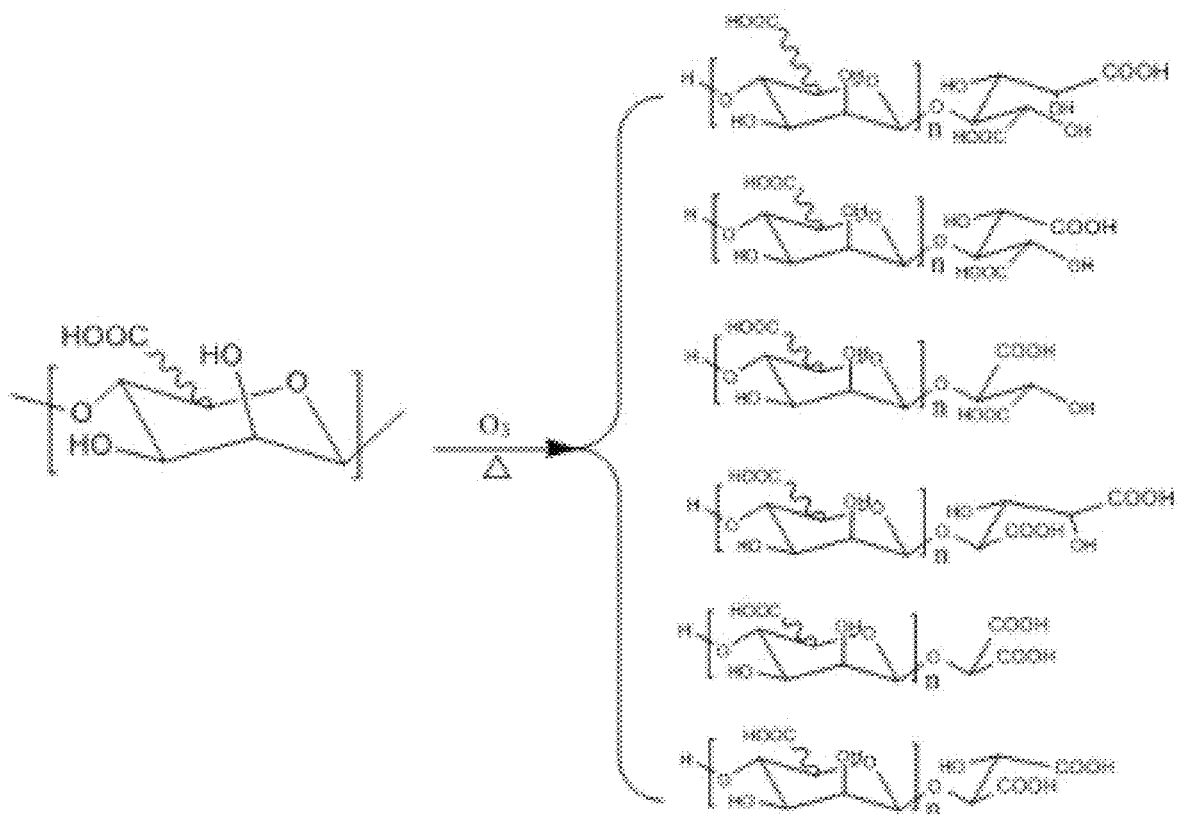
FIG. 24 shows the oxidative degeneration reaction process of the present invention.
Figure 24:
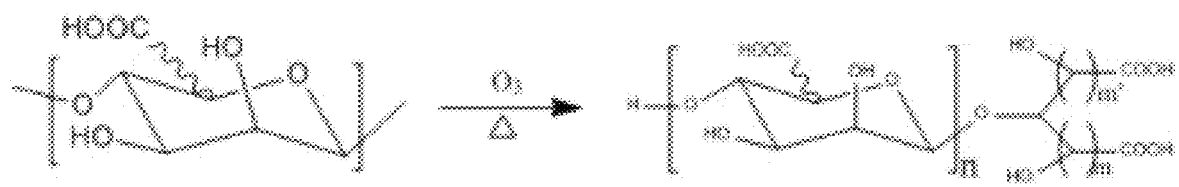

In the schematic diagram of FIG. 24 and compound of general formula (IV),

Oligosaccharides wherein m=2 and m'=1 are saccharic acids with 6 carbons at the end; Oligosaccharides wherein m=1 and m'=1 or m=2 and m'=0 are saccharic acids with 5 carbons at the end;

Oligosaccharides wherein m=1 and m'=0 or m=0 and m'=1 are saccharic acids with 4 carbons at the end;

Oligosaccharides wherein m=0 and m'=0 are saccharic acids with 3 carbons at the end.

In the composition, the total weight of alginic oligosaccharic diacids wherein n=1-5 accounts for 80-95% of the total weight of the composition, the total weight of alginic oligosaccharic diacids wherein n=1-3 accounts for 20-70% of the total weight of the composition, wherein the ratio of the total weight of alginic oligosaccharic diacids wherein n=1-3 to the total weight of alginic oligosaccharic diacids wherein n=4-7 is between 1.0 and 3.5, preferably between 1.0 and 3.0. The total weight of guluronic acids accounts for less than 50% of the total weight of the composition, preferably between 0.1% and 50%, most preferably between 1% and 30%.

In an exemplary embodiment, the preparation method of the present invention comprises the following steps:

(1) Preparation of Alginic Oligosaccharic Diacid Products:

Preparation of mixed polysaccharides of polymannuronic acid and polyguluronic acid. As described above, the raw material used in the present invention, mixed polysaccharides of polymannuronic acid and polyguluronic acid, can be prepared by a method known in the prior art, e.g., the methods disclosed in Chinese Patent Application No. 98806637.8 and CN02823707.2. A common method can be simply described below: alginic acid is preliminarily degraded to give mixed polysaccharides of polymannuronic acid and polyguluronic acid. After the mixed polysaccharides are subjected to acidic precipitation again, the content of part of the polyguluronic acid can be adjusted to obtain the mixed polysaccharides of polymannuronic acid and polyguluronic acid.

Ozone oxidative degradation. The mixed polysaccharides are dissolved in an appropriate amount of water and stirred at room temperature or under heating condition. With continuous introduction of ozone, the reaction starts. The pH value of the reaction can be adjusted to 3-13, preferably 4-10, more preferably 6-8 by dropwise adding dilute hydrochloric acid or dilute NaOH solution. The temperature is preferably 0-70° C., more preferably 10-45° C. After the completion of the reaction, the introduction of ozone is stopped and the pH is adjusted to neutral.

Membrane separation and purification. The reaction product obtained above is prepared into a solution at a concentration of about 10% and separated by a molecular cut-off membrane to remove degradation products below monosaccharide. The retentate is collected. The MWCO of the molecular cut-off membrane used is 1000 Da-3000 Da, preferably 2000 Da. The collected liquid is concentrated on a rotary evaporator and dried under vacuum to obtain an oligomeric alginic oligosaccharide mixture. After analysis, it is found that these products are all compositions of oligosaccharide from disaccharide to decasaccharide with contents being within certain proportion ranges. Examples 1-3 exemplarily show said method.

(2) Activity Comparison of the Oligosaccharide Compositions

The pharmacological activity of the oligosaccharide composition of the present invention is compared with the oligomannaric acid hexasaccharide in the prior application at the same time. The results show that the pharmacological activity of the oligosaccharide composition of the present invention is significantly higher than that of the oligomannaric acid hexasaccharide in the prior application. Without being bound by any theory, it is believed that when the proportion of disaccharide to hexasaccharide in the composition is higher than 60%, and the total weight of guluronic acid accounts for less than 50% of the weight of the composition, the composition is the most active; but when the proportion of guluronic acid exceeds 60%, the activity of the composition will also decrease.

The present invention also provides a medicament or health care product comprising the alginic oligosaccharide composition as described above and optionally a pharmaceutically acceptable carrier or excipient.

As described in Remington's Pharmaceutical Sciences, Martin, E.W., ed., Mack Publishing Company, 19th ed. (1995), methods for preparing oligosaccharide composition drugs comprising various proportions of active ingredients are known, or are obvious to those skilled in the art based on the disclosure of the present invention. The methods for preparing the pharmaceutical composition include incorporating appropriate pharmaceutical excipients, carriers, diluents and the like.

The pharmaceutical preparations of the present invention are prepared by known methods, including methods of conventional mixing, dissolving or lyophilization.

The pharmaceutical composition of the present invention is administered to patients by various routes suitable for the selected manner of administration, such as oral or parenteral (by intravenous, intramuscular, topical or subcutaneous routes).

Therefore, the composition drug of the present invention combined with a pharmaceutically acceptable carrier (such as an inert diluent or an edible carrier) can be administered systemically, for example, orally. They can be enclosed in hard or soft shell gelatin capsules and can be compressed into tablets. For oral therapeutic administration, the active compound of the present invention can be combined with one or more excipients and used as swallowable tablets, buccal tablets, lozenges, capsules, elixirs, suspensions, syrups, round tablets, etc. Such compositions and preparations should contain at least 0.1% of active compound. The proportion of such compositions and formulations can of course vary, and can comprise from about 1% to about 99% of the weight of a given unit dosage form. In such therapeutically useful compositions, the amount of active compound is such that an effective dosage level can be obtained.

Tablets, lozenges, pills, capsules, etc. may also comprise: binders, such as tragacanth, gum arabic, corn starch or gelatin; excipients, such as dicalcium phosphate; and disintegrants, such as corn starch, potato starch, alginic acid, etc.; lubricants, such as magnesium stearate; and sweeteners, such as sucrose, fructose, lactose, or aspartame; or flavoring agents, such as peppermint, wintergreen oil or cherry flavor. When the unit dosage form is a capsule, in addition to the above types of materials, it may also comprise a liquid carrier such as vegetable oil or polyethylene glycol. Various other materials may be present as coatings or otherwise modify the physical form of the solid unit dosage form. For example, tablets, pills or capsules can be coated with gelatin, wax, shellac or sugar. Syrups or elixirs may comprise active compounds, sucrose or fructose as sweeteners, methyl paraben or propyl paraben as preservatives, dyes and flavors (such as cherry flavor or orange flavor). Surely, any material used to prepare any unit dosage form should be pharmaceutically acceptable and non-toxic in the amount used. In addition, the active compound can be incorporated into sustained-release preparations and sustained-release devices.

The active compound can also be administered intravenously or intraperitoneally by infusion or injection. An aqueous solution of the active compound or its salt can be prepared, optionally with a miscible non-toxic surfactant. Dispersants in glycerin, liquid polyethylene glycol, triacetin and mixtures thereof and oils can also be prepared. Under ordinary conditions of storage and use, these preparations comprise a preservative to prevent the growth of microorganisms.

Pharmaceutical dosage forms suitable for injection or infusion may include a sterile aqueous solution or dispersant or a sterile powder of active ingredients (optionally encapsulated in liposomes) comprising immediate preparations suitable for sterile injectable or infusible solutions or dispersants. In all cases, the final dosage form must be sterile, liquid and stable under the conditions of manufacture and storage. The liquid carrier can be a solvent or a liquid dispersion medium, including, for example, water, ethanol, polyol (e.g., glycerol, propylene glycol, liquid polyethylene glycol, etc.), vegetable oil, non-toxic glyceride, and suitable mixtures thereof. The proper fluidity can be maintained, for example, by the formation of liposomes, by maintaining the required particle size in the case of dispersants, or by the use of surfactants. Various antibacterial and antifungal agents (such as parabens, chlorobutanol, phenol, sorbic acid, thimerosal, etc.) can be used to prevent microorganisms. In many cases, it is preferable to include isotonic agents, such as sugars, buffers or sodium chloride. Prolonged absorption of the injectable composition can be produced by using compositions that delay absorption (for example, aluminum monostearate and gelatin).

Sterile injectable solutions are prepared by combining the required amount of the active compound in a suitable solvent with the various other ingredients enumerated above as required, followed by filter sterilization. In the case of sterile powders for the preparation of sterile injectable solutions, the preferred preparation methods are drying in vacuum and lyophilization techniques, which will produce a powder of the active ingredient plus any otherwise required ingredients present in the previously sterile filtered solution.

Useful solid carriers include pulverized solids (such as talc, clay, microcrystalline cellulose, silica, alumina, etc.). Useful liquid carriers include water, ethanol or ethylene glycol or a water-ethanol/ethylene glycol mixture, and the combination drug of the present invention can be dissolved or dispersed in an effective content optionally with the help of a non-toxic surfactant. Adjuvants (such as fragrance) and additional antimicrobial agents can be added to optimize the properties for a given use.

Thickeners (such as synthetic polymers, fatty acids, fatty acid salts and esters, fatty alcohols, modified cellulose or modified inorganic materials) can also be used with liquid carriers to form coatable pastes, gels, ointment, soap, etc., which are directly applied to users' skin.

The therapeutically required amount of the compound or the mixture thereof depends not only on the compound itself, but also on the methods of administration, the nature of the disease to be treated, and the age and state of the patients, and ultimately depends on the decision of the physicians or clinicians present.

The above-mentioned preparations may be presented in a unit dosage form, which is a physically dispersed unit comprising a unit dose, suitable for administration to humans and other mammals. The unit dosage form can be a capsule or tablet, or a number of capsules or tablets. Depending on the specific treatment involved, the amount of the unit dose of the active ingredient can be varied or adjusted from about 0.1 to about 1000 mg or more.

Another aspect of the present invention provides a pharmaceutical composition or health care product, which comprises the alginic oligosaccharide composition of the present invention and an appropriate carrier if necessary.

Another aspect of the present invention provides a use of an alginic oligosaccharide composition to treat Alzheimer's disease.

Yet another aspect of the present invention provides a method for treating patients suffering from Alzheimer's disease, which comprises administering to the patients in need thereof an effective amount of the alginic oligosaccharide composition of the present invention.

Another aspect of the present invention provides a use of an alginic oligosaccharide composition to treat Parkinson's disease.

Yet another aspect of the present invention provides a method of treating patients suffering from Parkinson's disease, which comprises administering to the patients in need thereof an effective amount of the alginic oligosaccharide composition of the present invention.

Yet another aspect of the present invention provides a use of alginic oligosaccharide composition to treat inflammation.

Another aspect of the present invention provides a method for treating patients suffering from inflammation, which comprises administering to the patients in need thereof an effective amount of the alginic oligosaccharide composition of the present invention.

Another aspect of the present invention provides a use of alginic oligosaccharide composition to treat pain reactions.

Another aspect of the present invention provides a method for treating patients suffering from pain, which comprises administering to the patients in need thereof an effective amount of the alginic oligosaccharide composition of the present invention.

Another aspect of the present invention provides a use of alginic oligosaccharide composition to treat Diabetes Mellitus.

Another aspect of the present invention provides a method for treating patients suffering from Diabetes Mellitus, which comprises administering to the patients in need thereof an effective amount of the alginic oligosaccharide composition of the present invention.

Yet another aspect of the present invention provides a use of alginic oligosaccharide composition to treat vascular dementia.

Another aspect of the present invention provides a method for treating patients suffering from vascular dementia, which comprises administering to the patient in need thereof an effective amount of the alginic oligosaccharide composition of the present invention.

Pain mentioned in the present invention includes various pains, including acute pain, chronic pain, neuropathic pain, postoperative pain, chronic low back pain, cluster headache, herpes neuralgia, phantom limb pain, central pain, toothache, opioid-resistant pain, visceral pain, surgical pain, bone injury pain, fatigue and pain during childbirth, pain caused by burns including sunburn, postpartum pain, migraine, angina, and genitourinary tract related pain (including cystitis), vascular pain, trigeminal neuralgia, intercostal neuralgia, surgical incision pain, chronic fasciitis pain, heel pain, muscle pain, bone pain, joint pain, cancer pain, non-cancerous pain etc.

Inflammation mentioned in the present invention includes various inflammations, including but not limited to acute inflammation, chronic inflammation, vascular inflammation, neuroinflammation, central nervous system inflammation (such as multiple sclerosis, including encephalomyelitis, etc.), peripheral nerve inflammation, Arthritis (such as osteoarthritis, sacroiliitis, etc., psoriatic arthritis, rheumatoid arthritis, rheumatoid arthritis, etc.), ankylosing spondylitis, inflammatory bowel disease (such as Crohn's disease and ulcerative colon inflammation), inflammatory diabetic ulcers, systemic lupus erythematosus, inflammatory skin diseases (such as psoriasis, atopic dermatitis, eczema), etc.

The alginic oligosaccharide composition of the present invention is prepared by a method different from the prior art, in which it is not required to separate the M segment and the G segment. It greatly reduces the complexity of the production process and greatly reduces the production cost, and the preparation method involves simple reaction, high content of active ingredients, and no residual reaction reagents. It is proved through tests that the alginic oligosaccharide composition of the present invention has the potential to prevent and treat Alzheimer's disease, Diabetes Mellitus, Parkinson's disease, various inflammatory reactions, pain and vascular dementia.

Animal Models and Evaluation of Pharmacodynamic Activity

1. Animal model for anti-AD pharmacodynamic evaluation: Aβ unilateral ventricular injection was used to induce AD model, and Morris water maze was used to evaluate the learning and memory behavior of AD model rats.

Male Wistar rats (each weighing between 180-220 g) are taken and randomly divided into groups: sham operation control group, model group, dosing group, with 14 animals in each group. The rats were anesthetized by intraperitoneal injection of sodium pentobarbital (40 mg/kg) and fixed on a stereotaxic device. The skin was prepared and disinfected routinely, the skin was cut, bregma was exposed, and the positioning of CA1 area of the hippocampus was conducted with reference to "3.0 mm posterior bregma, 2.2 mm next to the midstitch, and 2.8 mm subdural" in "Rat Brain Stereotactic Atlas" (BAO Xinming, SHU Siyun, Beijing, People's Medical Press, 1991, 28). In each of the model group and the dosing group, a micro injector was used to insert the needle vertically into the skull in the CA1 area of the right hippocampus. 5 μl of condensed Aβ (Aβ1-40 was made with PBS solution into a solution of 1.4 mg/mL, which was incubated in a 37° C. incubator for 5 days to form aggregates) was slowly injected at a flow rate of 1 μL/min. After the injection was completed, the needle was retained for 5 minutes to fully diffuse Aβ, and then the needle was slowly withdrawn. The surgical incision was sutured and the rats were warmed to wake up. The control group was injected with the same amount of sterilized PBS, and the other steps were the same as the above. The corresponding drug was administered 7 days before the operation and was continued to be administered until the end of the test.

The Morris water maze test was performed on day 11 after the surgery.

Place navigation test: each group of rats was trained once a day for 5 consecutive days, i.e. place navigation test. The time it took for the animals to find the platform (ie, the escape incubation period) was recorded. If the platform was not found after about 90 s, they were guided to swim to the platform in a straight line and stand on the platform for 30 s to induce learning and memory.

Spatial probe test: one day after the place navigation test was completed, the platform was removed, and the rats were put into the water from the entry point, and the number of times they crossed the platform and the percentage of the swimming distance in the quadrant where the platform was located over the total distance were recorded. The learning and memory function of the animals were evaluated.

2. Animal Model for Anti-Parkinson's Disease (PD) Pharmacodynamic Evaluation

Mice were randomly divided into 8 groups: blank control group, MPTP model group and dosing group, with 14 animals in each group. Animals were divided into groups and given drugs on the same day. The blank control group and the MPTP model group were given saline solution by intragastric administration, and the other groups were given corresponding drugs once a day for 17 consecutive days. Modeling drugs were given from the 6th day. The animals in the blank control group were given 10 ml/kg of saline subcutaneously, and the other animals were given 25 mg/kg of MPTP subcutaneously once a day for five days.

Behavioral tests were carried out on the 11th, 14th and 17th days respectively. The mouse head was gently place upward on the rough top of the rod (diameter of 8 mm, height of 55 cm). The adjustment time of mice from head-up to head-down is the incubation period (T-turn), and the time of mice from downward movement to all limbs reaching the bottom of the rod was recorded as the climbing-down time (T-LA). More than 30 seconds would be recorded as 30 seconds. Each mouse was tested 5 times and the results were averaged.

MPTP has selective destructive effect on dopaminergic neurons in substantia nigra. MPTP-induced PD animal model is the most classical animal model similar to pathological changes and clinical characteristics of human Parkinson's disease. The main symptoms of PD are resting tremor, increased muscle tension, decreased movement, etc. The turning time and climbing-down time of rod climbing experiment can represent the overall activity and coordination ability of mice.

3. Animal Model for Anti-Inflammatory-Reaction Pharmacodynamic Evaluation (1) Rheumatoid Arthritis Model—Collagen-Induced Arthritis Mouse Model Male DBA/1 mice weighing 19-22 g were taken and randomly divided into groups: blank control group, model group, and dosing group, with 8 mice in each group. Except for the blank control group, the rest animals were immuno-sensitized by subcutaneous injection of 10 mg/kg bovine type II collagen-complete Freund's adjuvant (CII-CFA) emulsion at the tail root on day 0, and 1.5 mg/kg lipopolysaccharide (LPS) was injected intraperitoneally on day 23. The administration was started on day 28: the blank control group and the model group were given saline orally, and the other groups were given the corresponding drug (once a day for 14 consecutive days). After LPS injection, the mice were observed every day for disease conditions. When the mice began to develop the disease (occurrence of clinical symptoms of arthritis), according to the different degrees of the disease (redness, joint deformation) and based on the 0-4 point standard, clinical scoring was performed to reflect the degree of disease progression. 0 means no erythema and swelling; 1 means the occurrence of erythema or mild swelling near tarsal bones or near ankle joints or metatarsal bones, and redness and swelling at one toe; 2 means slight erythema and swelling of ankle joints and metatarsal bones, or redness and swelling at more than two toes; 3 means moderate erythema and swelling of ankle joints, wrist joints and metatarsal bones; 4 means severe redness and swelling at all of ankle joints, wrist joints, metatarsal bones and toes; the highest score for each limb is 4 points, and the highest score for each animal is 16 points.

(2) Multiple Sclerosis Model—MOG-Induced Multiple Sclerosis Mouse Model

Female C57BL/6 mice weighing 17-20 g were taken and 5 from them were randomly selected as a blank control group. The rest of the animals were immuno-sensitized by subcutaneous injection of myelin oligodendrocyte glycoprotein-complete Freund's adjuvant (MOG-CFA) emulsion on the back on day 0 (10 mg/kg MOG, 20 mg/kg CFA), and 10 ug/kg pertussis toxin was injected intraperitoneally on day 0 and day 2. The administration was started on day 1. The blank control group and the model group were given saline orally, and the other groups were given the corresponding drug (once a day for 24 consecutive days). About 12 days after the immunization, the immunized mice would develop symptoms. Close daily observation and recording of their weight and clinical scoring were started to reflect degrees of disease progression. 0-4 points are used to indicate different degrees: 0 means normal appearance without obvious disease signs; 1 means drooping and weak tail, and weakness of unilateral hind limb; 2 means drooping and weak tail, weakness of both hind limbs and staggering gait; 3 points means weakness and paralysis of unilateral hind limb; 4 means weakness and paralysis of both hind limbs.

(3) Systemic Lupus Erythematosus Model—MRL/lpr Lupus Erythematosus Mouse Model

MRL/lpr transgenic mice having homozygous mutations of Faslpr gene could spontaneously form lymphoid tissue hyperplasia. The mice began to develop symptoms of systemic lupus erythematosus at around 10-14 weeks of age. Female MRL/lpr transgenic mice (9 weeks old) were randomly divided into groups: blank control group, dosing group, with 8 mice in each group. The blank control group was given saline orally, and the other groups were given corresponding drug (once a day for 4 consecutive weeks). Lymph node scoring was performed once a week. 0-6 points indicate different degrees: 0 means normal; 1 means less than 1 cm in diameter at one point position on both sides; 2 means less than 1 cm in diameter at two point positions on both sides; 3 means less than 1 cm in diameter at three point positions on both sides; 4 means greater than 1 cm in diameter at one point position on both sides and less than 1 cm in diameter at the other two point positions on both sides; 5 means greater than 1 cm in diameter at two point positions on both sides, and less than 1 cm in diameter at another one point position on both sides; 6 means greater than 1 cm in diameter at three point positions on both sides.

(4) Inflammatory Bowel Disease (IBD) Model—Dextran Sulfate Sodium (DSS)-Induced Colitis Mouse Model Female C57 mice (7-8 weeks old) weighing 18-20 g were taken and randomly divided into groups: blank control group, model group, and dosing group, with 8 mice in each group. The mice in the model group and the dosing group were given 2.5% high-molecular-weight polymer dextran sulfate sodium (DSS) in the form of drinking water on days 1-7, and the administration was started on day 1. The control group and the model group were given saline orally, and the other groups were given corresponding drug (once a day for 30 consecutive days 0. On day 31, the mice were put to death by cervical dislocation, the abdominal cavities were opened, and the mesenteries were separated. The part from the beginning of the ileocecal area to the end of the anus in each mouse was taken. Each group was sampled sequentially. The length of the colon was measured.

4. Animal Model for Anti-Diabetes Mellitus Pharmacodynamic Evaluation

Male NIH mice were used and randomly divided into normal control group, model group, and dosing groups, with 10 in each group. On the test day, except for the normal group, the reset of the animals were intraperitoneally injected with 150 mg/kg streptozotocin. The corresponding drug was continuously given for 10 days. On day 11, the eyeballs were removed and blood was taken to measure the blood glucose concentration.

5. Animal Model for Anti-Pain Pharmacodynamic Evaluation (1) A Mouse Pain Model Induced by Acetic Acid Kunming mice, half of them male and half female, weighing 18-22 g, were randomly divided into groups: blank control group, model group, and dosing group, wherein there were 10 mice in each group. From the day of grouping, the blank control group was given intragastrically 20 ml/kg distilled water once a day for 7 consecutive days, and the other groups were dosed intragastrically with corresponding drugs once a day for 7 consecutive days. One hour after the last administration, the mice in each group were intraperitoneally injected with 0.2 ml of 0.6% acetic acid solution, and the incubation period of writhing (the time from the injection of acetic acid to the occurrence of writhing response) and the number of times of writhing in mice within 20 minutes after the injection of acetic acid were recorded.

The injection of chemicals such as acetic acid solution into the abdominal cavity of mice can stimulate the peritoneum of mice and cause intermittent persistent pain, which is manifested by recessed abdomen, front wall of abdomen being close to the bottom of the cage, crooked buttocks and extension of hind limbs, showing a special posture called a writhing response. The incubation period of writhing (the time from the injection of acetic acid to the occurrence of writhing response) and the number of times of writhing within a certain period of time can represent the severity of pain. The shorter the incubation period of writhing is and the more the number of times of writhing is, the more severe the pain is.

(2) A Migraine Rat Model Induced by Nitroglycerin

SD male rats, weighing 180-220 g, were randomly divided into groups: blank control group, model group, and dosing group, wherein there were 8 rats in each group. The administration was started on the day of grouping. The blank control group and the model group were given intragastrically distilled water once a day for 28 consecutive days, and the other groups were dosed intragastrically with the corresponding drugs once a day for 28 consecutive days. 30 minutes after the last administration, animals except the blank control group were given saline, and the other groups were injected subcutaneously with 10 mg/kg of nitroglycerin into the right shoulder to establish the model. The time of the appearance and duration of ear redness in rats after modeling, and the number of times of head-scratching within 30-45 minutes after modeling were observed. The content of 5-HT in brain tissue was determined by fluorescence spectrophotometry, and measured at Ex356 nm/Em 483 nm wavelength. The result is shown in ng/g brain weight.

Migraine is a dysfunction of blood vessels and nerves due to the interaction of blood vessels and nerve mechanisms. Nitroglycerin can cause the hypersensitivity of trigeminal nerve fibers and cause migraine by expanding the blood vessels of the meninges, forming neurogenic inflammation and activating the functions of hypothalamus, brainstem and spinal cord neurons. The nitroglycerin model is an animal model established in 1995 and has now become a classic animal migraine model. According to the pathogenic mechanism of nitroglycerin, the detection of the time of ear redness caused by vasodilation, the number of times of head scratching caused by pain and the content of serotonin (5-HT) (a pain sensitive factor in brain tissue) were used to assess the severity of migraine. The longer the ear redness lasts, the more times the head scratching and the higher the 5-HT content, the more severe the migraine is.

(3) A Migraine Rat Model Induced by Electrical Stimulation of the Trigeminal Ganglion SD rats, 5 months old, male, weighing 200-240 g, were randomly divided into groups: blank control group, sham operation group, model group, dosing group, wherein there were 10 rats in each group.

Each group was given corresponding drugs orally, and the blank control group, sham operation group, and model group were given distilled water orally. After continuous administration for 10 days, all rats except the blank control group were anesthetized by intraperitoneal injection of 350 mg/kg chloral hydrate. The rats were fixed on a stereotaxic apparatus, and a median incision was made on the top of the head. The skin and muscle were cut layer by layer to expose the skull at the middle of the sagittal suture. A dental drill was used to create a hole 3 mm back and 3 mm aside from the bregma, followed by inserting the electrode into the trigeminal ganglion (the depth from the dura is 9.5 mm). Anesthesia was continued after the surgery. All operations were performed under sterile conditions. The stimulation electrodes were debuged. The electrical stimulation parameters were 200 ms cycle, 10 v amplitude, and 5 ms wave width for 10 minutes stimulation. In the sham operation group, only the electrodes were inserted but no stimulation was given. 50 mg/kg Evans Blue was injected into the right femoral vein 7 minutes before stimulation, followed by perfusion and fixation within 20 minutes after stimulation.

Five minutes after the end of stimulation, the left ventricle was perfused for 2 minutes. Craniotomy was performed, and the whole brain was taken out, fixed for determining the c-fos in the pathological section by immunohistochemical. The electrode position was also determined, and the dura at the electrode insertion site and the corresponding site of the other cerebral hemisphere were separated, followed by washing with deionized water, spreading it flat on a glass slide, drying at 37° C. for 15 minutes, and fixing with 70% glycerol. The fluorescence intensity of the designated area on the stimulating side and the control side is detected under a confocal microscope with the excitation wavelength of 647 nm and the emission wavelength of 680 nm. The ratio of the fluorescence intensity of the stimulation side/control side is calculated to indicate the plasma protein extravasation (PPE). Continuous frozen coronal sections of the whole brain with a slice thickness of 10 μm were prepared, and the c-fos positive cells were labeled immunohistochemical fluorescence. 5 fields were randomly selected under a confocal microscope to determine the number of positive cells on the experimental side and the control side in caudal part of the spinal trigeminal nucleus, and then the average of the 5 fields was taken as the average number of positive cells.

The activation of the trigeminal neurovascular system is a key part in the production of pain in migraine patients, and the neuroinflammation of the meninges plays an important role in the production and maintenance of migraine pain. When the trigeminal nerve distributed in the dura mater is stimulated, it releases vasoactive substances, causing meningeal vasodilation, extravasation of plasma components, degranulation of mast cells and activation of platelets, resulting in migraine. In addition, the neurotransmitter released after pain stimulation binds to the corresponding receptors on the cell membrane. Under the action of the second messenger, the c-fos mRNA gene is expressed, translated and synthesized in the nucleus into c-fos protein, resulting in long-term physiological effects on the body. Therefore, during the occurrence of migraine, the number of cells expressing c-fos mRNA and c-fos protein in the spinal tract nucleus and raphe magnus of the trigeminal nerve increases. Therefore, the degree of migraine can be reflected by measuring the amount of serum protein exuded from the dura of migraine animals and the number of c-fos positive cells in caudal part (nucleus caudalis) of the spinal trigeminal nucleus. The lower the number of cells, the less severe the migraine is.

6. Animal Model for Anti-Vascular Dementia Pharmacodynamic Evaluation (1) A Mouse Model with Vascular Dementia Caused by Bilateral Common Carotid Artery Occlusion (BCCAo)

The bilateral common carotid artery occlusion (BCCAo) model is a commonly used vascular dementia model in the field established by global cerebral ischemia and reperfusion.

1.1 Animal Grouping and Administration

Male C57BL/6 mice, weighing 22±2 g were chosen and randomly divided into groups: sham operation group, 30-minute bilateral common carotid artery occlusion (BCCAo) model group (abbreviated as 30-min BCCAo group), and dosing group, wherein there were 10 animals in each group. After the animals were divided into groups, mice in the sham operation group and 30-min BCCAo group were given intragastrically distilled water, once a day, for 5 consecutive days, followed by BCCAo surgery. Mice in the dosing group were dosed intragastrically with the corresponding drugs, once a day, for 5 consecutive days, followed by BCCAo surgery. The BCCAo surgery was to anesthetize each group of mice with pentobarbital sodium; separate and occlude the bilateral common carotid arteries of the mice in the model group and the dosing group for 30 minutes, then remove the occlusion and suture the neck wound. For the sham operation group, the bilateral common carotid arteries were not occluded after separation, and the neck incision was directly sutured. Twenty-four hours after BCCAo, mice in each group continued to be given intragastrically the corresponding drugs or distilled water according to the preoperative dosing schedule, for further 23 consecutive days of administration. The darkness avoidance test was performed on the 7th day after BCCAo, and the Morris water maze test was started on the 13th day to evaluate the improvement effect of the mannuronic diacid composition on the learning and memory ability of mice. After the behavioral test, the mice were sacrificed, and the brain tissues were fixed. The neuronal damage in the hippocampus of the mice after BCCAo and the protective effect of the mannuronic diacid composition on the injured neurons were evaluated by the methods such as HE staining.

1.2 Darkness Avoidance Test

The darkness avoidance test is used to test the learning and memory abilities of mice in spatial discrimination. The memory impairment of spatial positioning can only appear when the hippocampus or the area around the hippocampus is damaged. The dark-avoidance experimental box is a device designed to take advantage of the habit of following darkness and avoiding light in mice. Half of the box is a dark room and the other half is a bright room, with a small hole in the middle for connection. The bottom of the dark room is covered with a copper grid. Animals are shocked when they enter the dark room, and escape back to the light room. After the animals are trained for 24 hours, the test is performed again. The incubation period in the darkness avoidance test refers to the time from when the animal is placed in the light room to the first time it enters the dark room. The longer the incubation period in the darkness avoidance test is and the fewer the number of avoidance mistake is, the better the animal memory is.

1.3 Morris Water Maze Behavior Assay

The Morris water maze (MWM) test is an experiment in which experimental animals are forced to swim and learn to find platforms hidden in the water. It is mainly used to test the experimental animals' ability of learning and memory in terms of spatial position and direction (spatial positioning). The mouse Morris water maze is mainly composed of a cylindrical pool with a diameter of 80 cm and a height of 70 cm and a movable platform with a diameter of 8 cm. The digital camera in the sky above the pool is connected to a computer. Before the test, clean water is poured into the pool in advance. The water depth is 15 cm, and the water surface is 0.5 cm above the surface of the platform. Milk is added to make the pool water opaque. The position of the platform remains unchanged during the test. Morris water maze behavior includes the following two test indicators.

The place navigation test is used to measure the ability of mice to learn the water maze and acquire memory. The test was started on the 13th day after BCCAO and lasted 4 days. The mice were trained once both in the morning and in the afternoon, totally 8 times. During training, the mouse enters the pool at ½ arc in the west quadrant, and enters the water with its head toward the pool wall. If the platform is not found within 120 seconds, the experimental staff will lead it to the platform and leave it for 30 seconds to guide its learning and memory. The route map and the time required for the mice to find and climb on the platform are observed and recorded, i.e., recording their escape incubation period and swimming speed in Morris water maze test. The escape incubation period in the Morris water maze test refers to the time from when the mouse enters the water to find the platform. The shorter the escape incubation period in the Morris water maze test is, the better the animal memory is.

Spatial probe test is used to measure the ability of mice to retain the memory of the platform's spatial location after learning to find the platform. After the place navigation test was finished, the platform was removed at 1 day intervals. The mice were put into the water from the same entry point, and the number of times they crossed the original platform was measured. Data acquisition and processing were completed by the image automatic monitoring and processing system.

(2) A Rat Model with Vascular Dementia Caused by Middle Cerebral Artery Occlusion (MCAO)

The middle cerebral artery occlusion (MCAO) model is a vascular dementia model commonly used in the field established by focal cerebral ischemia.

2.1 Animal Grouping and Administration

Male Wistar rats were chosen and randomly divided into groups: blank control group, sham operation group, model group (MCAO group), and dosing group, wherein there were 10 animals in each group. Animals in the blank group, sham operation group, and MCAO group were orally given distilled water, and the algin oligosaccharide group were all orally given the corresponding dose of algin oligosaccharide. After 7 days of continuous administration in each group, except for the rats in the blank group, the rats in the other groups were anesthetized by intraperitoneal injection of 350 mg/kg chloral hydrate, and fixed on the rat board in the left lateral position. Under an operating microscope, the skin was incised along the midpoint of the connection between the external auditory canal and the eye canthus to expose the zygomatic arch. The distance between the phosphate bone and the mandible was spread using a small distractor. A 2 mm×2 mm bone window was opened at the base of the skull. The dura mater was opened to expose the middle cerebral artery, and one side of the middle cerebral artery was coagulated by high-frequency electrocautery to cause local cerebral ischemia (the animals in the sham operation group only exposed the middle cerebral artery without coagulation). The incision was sutured layer by layer. The room temperatures during and after the operation were strictly controlled at 24-25° C. After surgery, the drug or distilled water were continued to give to each group according to the preoperative dosing schedule. The Morris water maze test was performed for each group on the 11th day after the surgery.

In this experiment, rats in each group were trained once a day for 5 consecutive days, i.e., place navigation test. The time it took for the animals to find the platform (i.e., the escape incubation period in the Morris water maze test) was recorded. Those who failed to find the platform for about 120 seconds were guided to swim toward the platform in a straight line and stand on the platform for 30 seconds to induce learning and memory. After the place navigation test was finished, the platform was removed at 1 day intervals. The rats were put into the water from the entry point, and the time they first reached the original platform and the number of times they crossed the original platform were recorded, i.e., spatial probe test. The learning and memory function of animals were evaluated. The escape incubation period in the Morris water maze test refers to the time from when the rat enters the water to find the platform. The shorter the escape incubation period in the Morris water maze test is, the better the animal memory is.

Advantages of the present invention are further illustrated in the following nonlimiting examples. However, the specific materials and amounts thereof as well as other experimental conditions used in the examples should not be construed as limiting the present invention. Unless otherwise specified, the parts, proportions, percentages, and the like in the present invention are all calculated by mass.

Example 1

Step 1): Preparation of an Alginic Acid Oligosaccharide Mixture

5 Kg of sodium alginicate was prepared into a solution of about 10%, and the pH was adjusted to about 3.0 by adding dilute hydrochloric acid. The solution was heated to 80° C., and stirred. It was allowed to react for 10 hr before the heating was stopped. After cooling to room temperature, the pH was adjusted to 9.0 by adding NaOH, and further adjusted to 3.2 by adding dilute hydrochloric acid. The solution was centrifuged at 5000 rpm for 10 min. The supernatant was collected, and adjusted to pH 1.0 by adding HCl. After centrifugation, the precipitate was collected, concentrated on a rotary evaporator, and dried under vacuum to give 1500 g of the intermediate.

See FIG. 1 for the NMR spectrum of the intermediate. The NMR measuring method is as follows: sample preparation: 30 mg of the sample to be tested was weighed and dissolved in 0.5 ml D2O, and lyophilized; 0.5 ml deuterated heavy water was further added for dissolution; lyophilization was performed again; and finally, the lyophilized sample powder was dissolved with an appropriate amount of heavy water, transferred to an NMR tube, and prepared to a 100 mg/ml solution to be tested; 0.01% (w/v) deuterated TSP (trimethylsilylpropionic) sodium salt was added as an internal standard. Nuclear magnetic data acquisition and processing: 400M Fourier transform nuclear magnetic resonance instrument collected one-dimensional hydrogen spectrum at 60° C. The pulse sequence was 45° pulses, each acquisition was 4 seconds, the relaxation time was 1 second, and the accumulation was 20 times, and the spectral width was from −2 ppm to 10 ppm. After data collection, Fourier transform was used to obtain a one-dimensional hydrogen spectrum, and the TSP methyl hydrogen signal was set to 0.00 ppm.

It can be seen from FIG. 1 that the intermediate contained a mannuronic acid segment (M-block, chemical shift 5.1 ppm) and a guluronic acid segment (G-block, chemical shift 5.5 ppm), as well as a chimeric segment of mannuronic acid and guluronic acid (MG-block, chemical shift 5.3 ppm). 500 g of the intermediate was weighed, and dissolved in distilled water to prepare a solution in a volume of 5 L. The solution was adjusted to pH 6.5 with NaOH, and heated in a water bath to control the reaction temperature at 75° C. The gas flow rate at the outlet of an oxygen cylinder and the power of an ozone generator were adjusted such that ozone was fed into the reaction solution at a mass concentration flow rate of 8 g/hr. After 4 hr of reaction, the feeding of ozone was stopped, and a suitable amount of water was added to adjust the concentration of the solution to about 10%. The solution was filtered through an ultrafiltration membrane with a molecular weight cut-off of 2,000 Da to collect a retentate. The collected liquid was concentrated on a rotary evaporator and dried under vacuum to obtain 350 g of product A.

Step 2): Analysis of Proportions and Structures of Oligosaccharides with Various Polymerization Degrees in Alginic Oligosaccharic Diacid Product a 100 mg of the above dried alginic oligosaccharic diacid product A was accurately weighed, dissolved in water to a concentration of 10 mg/mL, and passed through a 0.22 um filter membrane to obtain a test sample solution. The proportions of oligosaccharides with different polymerization degrees in the composition were determined by Superdex peptide molecular exclusion chromatography (GE Co.) in combination with multi-angle laser light scattering (MALS, Wyatt Co.). The experimental conditions were as follows:

Chromatographic column: Superdex peptide 10/300G1
Mobile phase: 0.1 mol/L NaCl
Injection volume: 10 μL
Flow rate: 0.3 mL/min Test results: from disaccharide to decasaccharide were represented by dp2-dp10, respectively, dp2 was 18%, dp3 was 24%, dp4 was 23%, dp5 was 14%, dp6 was 8%, dp7 was 7%, dp8 was 2%, dp9 was 2% and dp10 was 2%.

Step 3): LC-MS Analysis of Structures of Oligosaccharides with Various Polymerization Degrees in Alginic Oligosaccharic Diacid Product A Experimental Conditions:
Chromatographic column: Superdex peptide 10/300G1
Mobile phase: 20% methanol+80% 80 mmol/L NH4Ac
Flow rate: 0.1 mL/min
Column temperature: 25° C.±0.8° C.
Mass spectrometry conditions: Agilent 6540 QTOF; ion source: ESI collision voltage 120 V; negative ion mode. The width of the acquired signal (m/z) was 100-1000.

Figure 2:
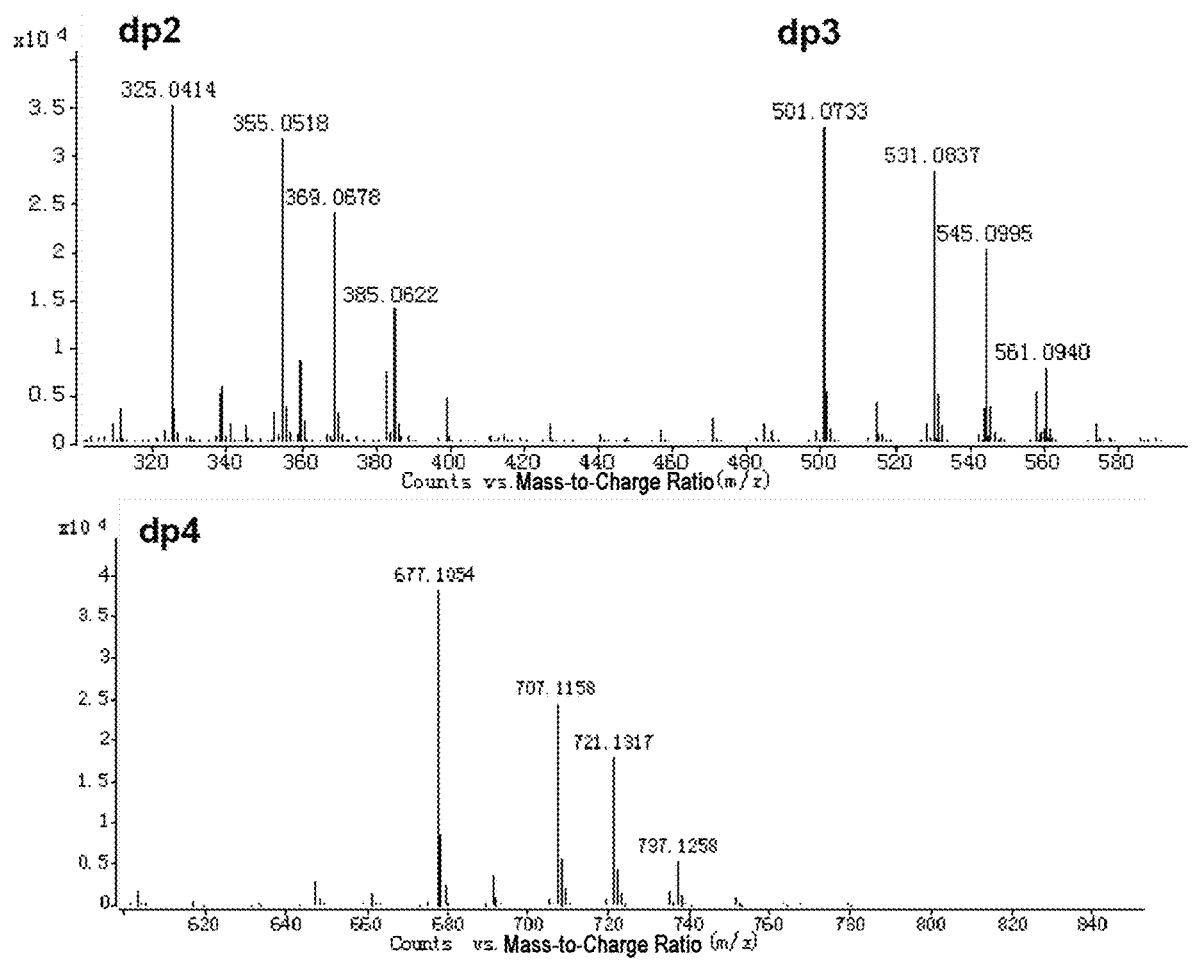
FIG. 2 shows mass spectra of disaccharide, trisaccharide and tetrasaccharide in product A.
Figure 3:
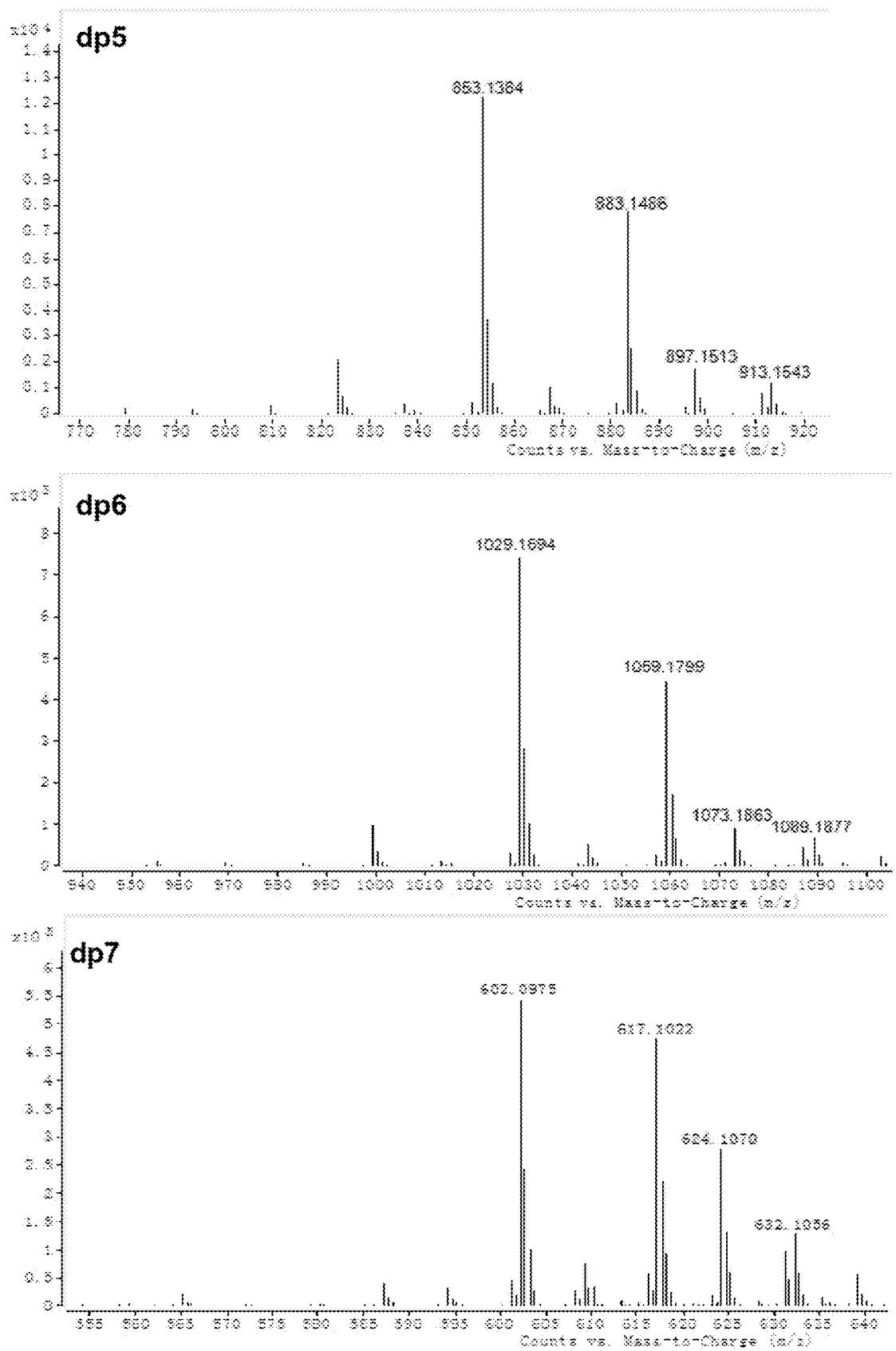
FIG. 3 shows mass spectra of pentasaccharide, hexasaccharide and heptasaccharide in product A.
Figure 4:
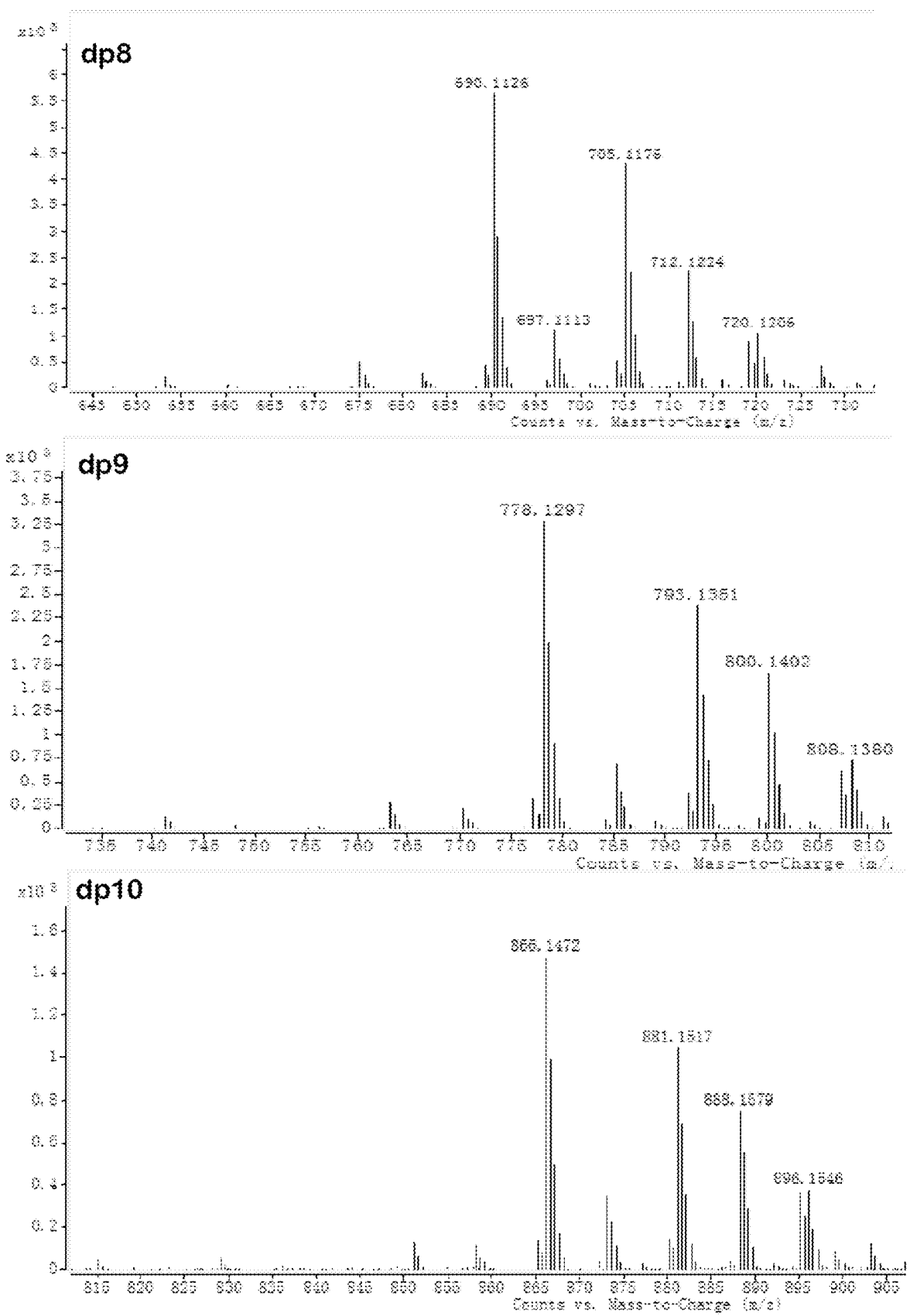
FIG. 4 shows mass spectra of octasaccharide, nonasaccharide and decasaccharide in product A.
Figure 5:
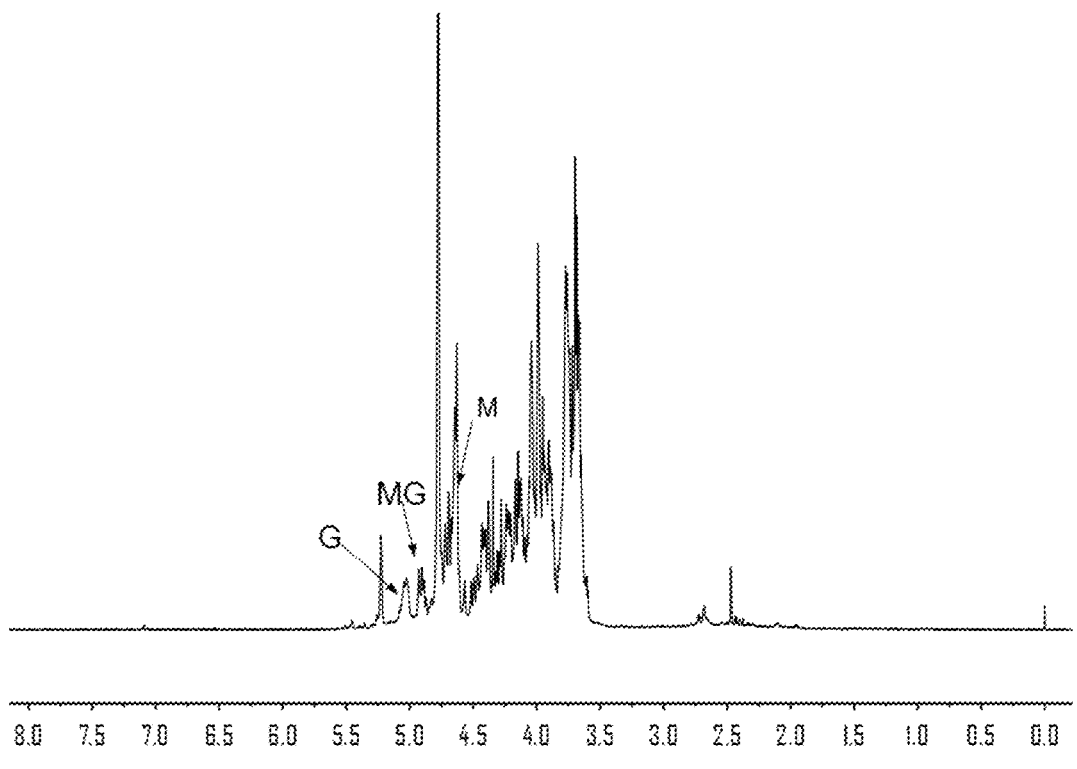
FIG. 5 shows NMR spectrum of product A.

The mass spectra of oligosaccharides with various polymerization degrees are shown in FIGS. 1-3. Various signal peaks in the mass spectra were assigned, confirming the molecular structure of all oligosaccharides in product A, i.e., the structure shown in General Formula (III). See Table 1 below for the signal assignments and the structures corresponding to the signals.

was used to obtain a one-dimensional hydrogen spectrum, and the TSP methyl hydrogen signal was set to 0.00 ppm. The proton nuclear magnetic resonance spectrum of product A is shown in FIG. 5. In FIG. 5, the multiplet with a

TABLE 1 six diacid structures in oligosaccharides with different polymerization degrees in product A and their mass-to-charge ratios in mass spectra

| No. | Molecular Structure | Molecular Formula | Mass-to-Charge Ratio (m/z) | | | | | | | | |
|---|---|---|---|---|---|---|---|---|---|---|---|
| | | | n = 1 [M-1]⁻ | n = 2 [M-1]⁻ | n = 3 [M-1]⁻ | n = 4 [M-1]⁻ | n = 5 [M-1]⁻ | n = 6 [M-1]⁻ | n = 7 [M-2]²⁻ | n = 8 [M-2]²⁻ | n = 9 [M-2]²⁻ |
| 1 | [structure] | $(C_6H_8O_6)_n C_6H_{10}O_8$ n = 1-9 | 385 | 561 | 737 | 913 | 1089 | 1265 | 720 | 808 | 896 |
| 2 | [structure] | $(C_6H_8O_6)_n C_5H_8O_7$ n = 1-9 | 355 | 531 | 707 | 883 | 1059 | 1235 | 705 | 793 | 881 |
| 3 | [structure] | $(C_6H_8O_6)_n C_5H_8O_7$ n = 1-9 | 355 | 531 | 707 | 883 | 1059 | 1235 | 705 | 793 | 881 |
| 4 | [structure] | $(C_6H_8O_6)_n C_4H_6O_6$ n = 1-9 | 325 | 501 | 677 | 853 | 1029 | 1205 | 690 | 778 | 866 |
| 5 | [structure] | $(C_6H_8O_6)_n C_4H_6O_6$ n = 1-9 | 325 | 501 | 677 | 853 | 1029 | 1205 | 690 | 778 | 866 |
| 6 | [structure] | $(C_6H_8O_6)_n C_3H_{10}O_5$ n = 1-9 | 295 | 471 | 647 | 823 | 999 | 1175 | 675 | 763 | 851 |

It was found from the above mass spectrometric structural analysis that the mannuronic acid or the guluronic acid at the reducing end of the sugar chain in product A was oxidized to a saccharic acid structure (see General Formula IV for the structure), which could be a mannaric acid or guluronic acid structure comprising 6 carbon atoms (m+m'=3) with a content of about 10%-30%, or a decarboxylation product of mannaric acid or guluronic acid, i.e., a saccharic acid comprising 5 carbons (m+m'=2) (30-50%) and a saccharide diacid with 4 carbons (m+m'=1) (30%-40%).

Step 4) NMR Analysis of Guluronic Acid Content in Alginic Oligosaccharic Diacid Product A Sample preparation: 50 mg of the sample to be tested was weighed, dissolved in 0.5 ml D2O, and lyophilized; 0.5 ml deuterated heavy water was added for dissolution; lyophilization was again performed; finally, the lyophilized sample powder was dissolved with an appropriate amount of heavy water, all of which was transferred to an NMR tube and prepared to a 100 mg/ml solution to be tested; and 0.01% (w/v) deuterated TSP (trimethylsilylpropionic) sodium salt was added as an internal standard.

Nuclear magnetic data acquisition and processing: 400M Fourier transform nuclear magnetic resonance instrument collected one-dimensional hydrogen spectrum at room temperature. The pulse sequence was 45° pulses, each acquisition was 4 seconds, the relaxation time was 1 second, and the accumulation was 20 times, and the spectral width was from −2 ppm to 10 ppm. After data collection, Fourier transform chemical shift of 4.6 ppm is the hydrogen signal at C-1 position of mannuronic acid (M), 5.0 ppm is the hydrogen signal at C-1 position of guluronic acid (G), 4.9 ppm is the C-1 hydrogen signal of chimeric segment of mannuronic acid and guluronic acid (MG). The formula for calculating the content of guluronic acid is:

$$G\% = \frac{I_{5.0} + 0.5 I_{4.9}}{I_{5.8} + I_{4.6} + I_{4.9}} \times 100\%$$

In the above formula, 14.6, 15.0 and 14.9 are respectively the hydrogen signal integral values at the C-1 positions of the mannuronic acid (M), the guluronic acid (G), the chimeric segment of mannuronic acid and guluronic acid chimeric (MG). By calculation, the content of the guluronic acid in A is 30%.

Example 2

100 g of commercially available sodium alginate (purchased from the website of Sinopharm Reagent Co., CAS No. 9005-38-3, specification CP, Shanghai tested) was weighed, mixed evenly upon addition of distilled water, and was prepared into a solution with a volume of 0.8 L after swelling. The solution was adjusted to pH 4.0 with NaOH, and the reaction was carried out at room temperature (25° C.). The gas flow rate at the outlet of an oxygen cylinder and the power of an ozone generator were adjusted such that ozone was fed into the reaction solution at a mass concentration flow rate of 1 g/hr. After 10 hr of reaction, the feeding of ozone was stopped, and a suitable amount of water was added to adjust the concentration of the solution to about 15%. The solution was filtered through an ultrafiltration membrane with a molecular weight cut-off of 1,000 Da to collect a retentate. The collected liquid was concentrated on a rotary evaporator and dried under vacuum to obtain 80 g of product B.

The proportions of oligosaccharides components with various polymerization degrees in B were determined by Superdex peptide molecular exclusion chromatography (GE Co.) in combination with multi-angle laser light scattering (MALS, Wyatt Co.). The measuring method was the same as the relevant part in example 1. Test results: from disaccharide to decasaccharide were represented by dp2-dp10, respectively, dp2 was 25%, dp3 was 24%, dp4 was 18%, dp5 was 13%, dp6 was 10%, dp7 was 5%, dp8 was 2%, dp9 was 2% and dp10 was 1%.

Figure 6:
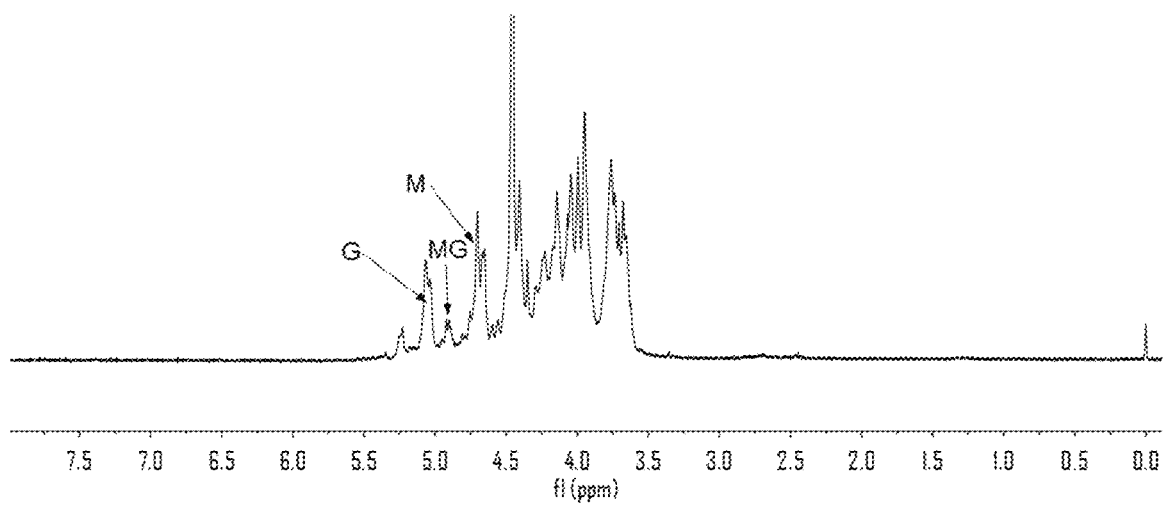
FIG. 6 shows NMR spectrum of product B.

The guluronic acid content in product B was determined to be 50% at 60° C. using a 400M Fourier transform nuclear magnetic resonance instrument. The measuring method was the same as that in the relevant part of example 1. The proton nuclear magnetic resonance spectrum is shown in FIG. 6. It can be seen from the figure that the integrated area of mannuronic acid (M, chemical shift value 4.6 ppm) and guluronic acid (G, chemical shift value 5.0 ppm) are relatively close, while the integral area of the chimeric segment of mannuronic acid and guluronic acid (MG, chemical shift of 4.9 ppm) is small. According to the formula for calculating the content of guluronic acid product (G), the content of G is 50%.

Example 3

100 g of the intermediate of example 1 was weighed. After addition of water for suspension, NaOH was added to adjust the pH value to basic to allow full dissolution of the powder. The solution was eventually prepared into a solution of 1 L, and HCl was further added to adjust the pH value to 2.95. Part of white precipitates appeared, which was removed via centrifugation. The supernatant was collected. Distilled water was added for further dilution until a solution with a volume of 1.5 L was prepared. The solution was adjusted to pH 9.0 with NaOH, and the reaction was carried out in a water bath at 45° C. The gas flow rate at the outlet of an oxygen cylinder and the power of an ozone generator were adjusted such that ozone was fed into the reaction solution at a mass concentration flow rate of 3 g/hr. After 2 hr of reaction, the feeding of ozone was stopped, and a suitable amount of water was added to adjust the concentration of the solution to about 5%. The solution was filtered through an ultrafiltration membrane with a molecular weight cut-off of 3,000 Da to collect a retentate. The collected liquid was concentrated on a rotary evaporator and dried under vacuum to obtain 60 g of product C.

The proportions of oligosaccharides with various polymerization degrees in C were determined by Superdex peptide molecular exclusion chromatography (GE Co.) in combination with multi-angle laser light scattering (MALS, Wyatt Co.). The measuring method was the same as the relevant part in example 1. Test results: from disaccharide to decasaccharide were represented by dp2-dp10, respectively, dp2 was 9%, dp3 was 21%, dp4 was 27%, dp5 was 18%, dp6 was 13%, dp7 was 6%, dp8 was 3%, dp9 was 2%, and dp10 was 1%.

Figure 7:
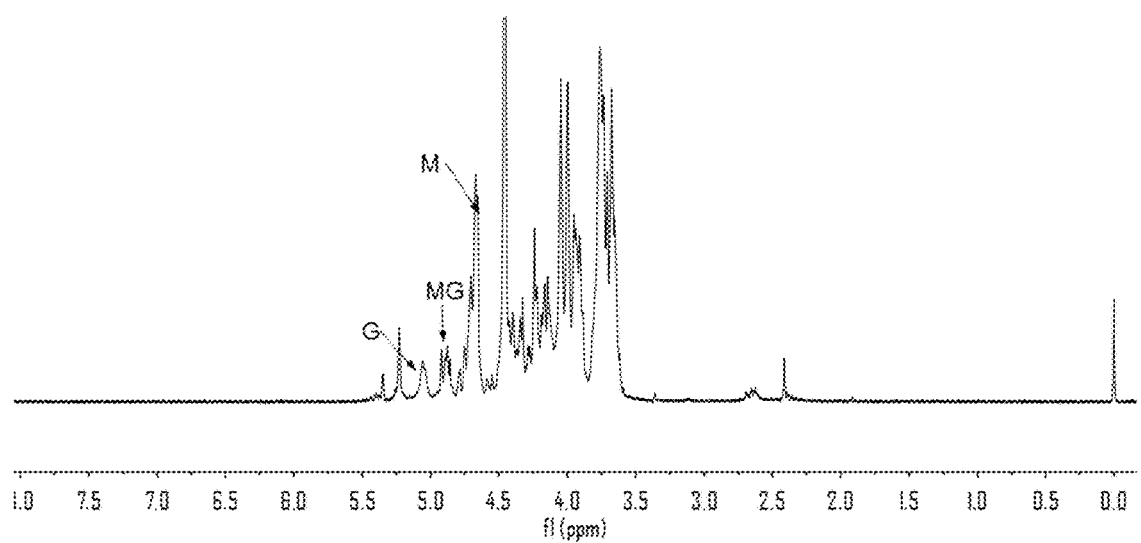
FIG. 7 shows NMR spectrum of product C.

The content of guluronic acid in product C was determined to be 10% using a 400M Fourier transform nuclear magnetic resonance instrument at 60° C., and the determination method was the same as that in the relevant part of example 1. The test results are shown in FIG. 7. By integrating the corresponding signals separately, the integrated area of the mannuronic acid (M, chemical shift value 4.6 ppm) is 13 times the integrated area of the guluronic acid (G, chemical shift value 5.0 ppm), and the integrated area of the chimeric segment of the mannuronic acid and the guluronic acid (MG, chemical shift 4.9 ppm) is close to that of the guluronic acid. According to the formula for calculating the content of the guluronic acid product (G) shown in example 1, the content of G is 10%.

Example 4

Evaluation of the Pharmacological Activity Between Alginic Oligosaccharic Diacid Composition and the Mannuronic Diacid Hexasaccharide.

Sample Preparation:

1. The Preparation of the Mannuronic Diacid Hexasaccharide

With reference to the methods disclosed in examples 1 and 2 of the prior patent 200580009396.5, 20 g of the mannuronic diacid hexasaccharide, was prepared.

The oligosaccharide proportions and guluronic acid contents of the products A, B, and C prepared in the foregoing examples 1, 2, and 3 of the present application are shown in Table 2 below.

2. Preparation of Product D

A product with high G content was prepared with reference to the preparation method of example 2 above. The sodium alginate raw material was a sample with high G content provided by Qingdao Haizhilin Biotechnology Development Co., Ltd., and the preparation method was the same as the corresponding part of example 2. Specifically, 500 g of sodium alginate powder with high G content was evenly mixed with distilled water, and was prepared into a solution of 5 L volume after swelling, and then adjusted to pH 4.0 with NaOH, and reacted at room temperature 25° C. The gas flow rate at the outlet of an oxygen cylinder and the power of an ozone generator were adjusted such that ozone was fed into the reaction solution at a mass concentration flow rate of 1 g/hr. After 12 hr of reaction, the feeding of ozone was stopped, and a suitable amount of water was added to adjust the concentration of the solution to about 15%. The solution was filtered through an ultrafiltration membrane with a molecular weight cut-off of 1,000 Da to collect a retentate. The collected liquid was concentrated on a rotary evaporator and dried under vacuum to obtain 350 g of product D.

The proportions of oligosaccharides components with various polymerization degrees in D were determined by Superdex peptide molecular exclusion chromatography (GE Co.) in combination with multi-angle laser light scattering (MALS, Wyatt Co.). The measuring method was the same as the relevant part in example 1. Test results: from disaccharide to decasaccharide were represented by dp2-dp10, respectively, dp2 was 18%, dp3 was 26%, dp4 was 20%, dp5 was 15%, dp6 was 8%, dp7 was 7%, dp8 was 3%, dp9 was 2% and dp10 was 1%.

Figure 8:
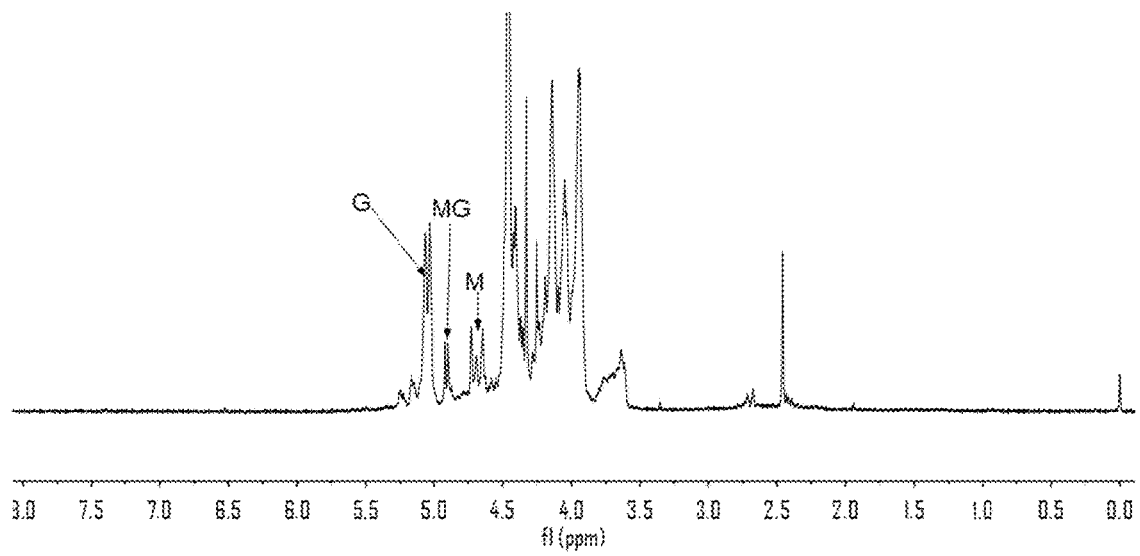
FIG. 8 shows NMR spectrum of product D.

The guluronic acid content in product D was determined to be 60% at 60° C. using a 400M Fourier transform nuclear magnetic resonance instrument. The measuring method was the same as that in the relevant part of example 1. The hydrogen nuclear magnetic resonance spectrum is shown in FIG. 8. It can be seen from the figure that the integrated area of the guluronic acid (G, chemical shift value 5.0 ppm) is bigger than that of the mannuronic acid (M, chemical shift value 4.6 ppm), while the integral area of the chimeric segment of the mannuronic acid and the guluronic acid (MG, chemical shift of 4.9 ppm) is smaller. According to the formula for calculating the content of guluronic acid product (G) in example 1, the content of G is 60%.

TABLE 2 percentages of oligosaccharides and the content of the guluronic acid in alginic diacid oligosaccharides composition products

| Proportion Composition | Di-saccharide | Tri-saccharide | Tetra-saccharide | Penta-saccharide | Hexa-saccharide |
|---|---|---|---|---|---|
| A | 18% | 24% | 23% | 14% | 8% |
| B | 25% | 24% | 18% | 13% | 10% |
| C | 9% | 21% | 27% | 18% | 13% |
| D | 18% | 26% | 20% | 15% | 8% |

| Proportion Composition | Hepta-saccharide | Octa-saccharide | Nona-saccharide | Deca-saccharide | Guluronic Acid Content |
|---|---|---|---|---|---|
| A | 7% | 2% | 2% | 2% | 30% |
| B | 5% | 2% | 2% | 1% | 50% |
| C | 6% | 3% | 2% | 1% | 10% |
| D | 7% | 3% | 2% | 1% | 60% |

10 g of each of the above four samples A, B, C and D and the mannuronic diacid hexasaccharide sample were taken out. According to the methods described in the "animal model for anti-AD pharmacodynamic evaluation", the "animal model for anti-PD pharmacodynamic evaluation", the "animal model for anti-inflammatory-reaction pharmacodynamic evaluation", the "animal model for anti-Diabetes Mellitus pharmacodynamic evaluation", the "animal model for anti-pain pharmacodynamic evaluation", and the "animal model for anti-vascular dementia pharmacodynamic evaluation", the pharmacological activities of these alginic oligosaccharic diacid compositions were compared with the pharmacological activity of the mannuronic diacid hexasaccharide.

1. Evaluation of Anti-AD Pharmacodynamic Evaluation

In the test, compared with the sham operation control group, the model group had a significantly longer incubation period to find the platform, indicating that the evaluation model was successful established. Compared with the model group, the incubation period for finding the platform in each dosing group was significantly shorter.

Figure 9:
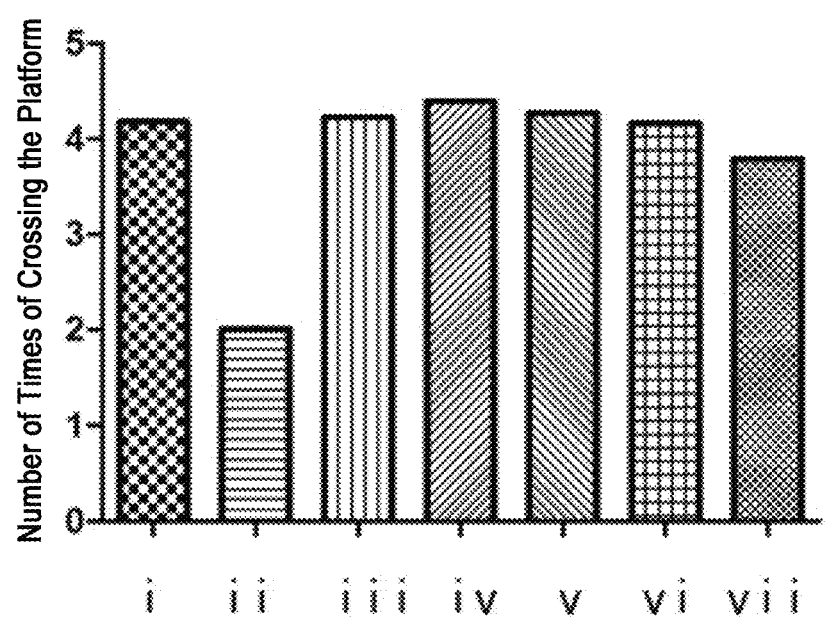
FIG. 9 shows the effects of different oligosaccharide compositions and the mannuronic diacid hexasaccharide on the number of times of crossing platform in AD animals. The samples corresponding to the numbers on the abscissa in the Figure are the following: i: control group; ii: model group; iii: product A; iv: product B; v: product C; vi: product D; vii: the mannuronic diacid hexasaccharide.
Figure 10:
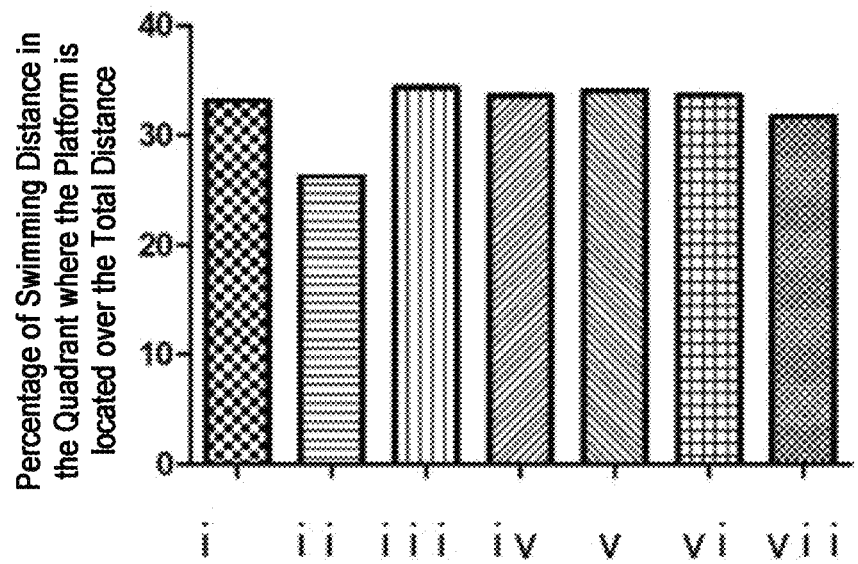
FIG. 10 shows the effects of different oligosaccharide compositions and the mannuronic diacid hexasaccharide on swimming distance of AD animals; wherein the symbols on the abscissa of the Figure are the same as those in FIG. 9.

One day of rest after the place navigation test was completed, the platform was removed, and spatial probe test was started. The number of times the animals crossed the platform and the percentage of the swimming distance in the quadrant where the platform was located over the total distance were observed and determined. The learning and memory function of the animals were evaluated. The results showed that compared with the sham operation control group, the number of times of crossing the platform was significantly reduced in the model group, and the number of times of crossing the platform was significantly increased in the dosing group, as shown in FIG. 9. The percentage of the swimming distance in the quadrant where the original platform was located over the total distance had a similar trend with the number of times of crossing the platform. Compared with the sham operation control group, the percentage of the swimming distance in the quadrant where the original platform was located over the total distance was significantly reduced in the model group, and the percentage of the swimming distance in the quadrant where the original platform was located over the total distance in the dosing group increased significantly, as shown in FIG. 10.

The test results showed that the pharmacodynamic activities of products A, B, and C were stronger than that of the mannuronic diacid hexasaccharide, indicating that the oligosaccharide composition comprising a certain amount of guluronic acid and having a proportion of disaccharide to hexasaccharide of higher than 60% had a synergistic effect. However, the activity of the oligosaccharide composition D with a higher content of guluronic acid decreased.

2. Evaluation of Anti-PD Pharmacodynamic Evaluation

Figure 11:
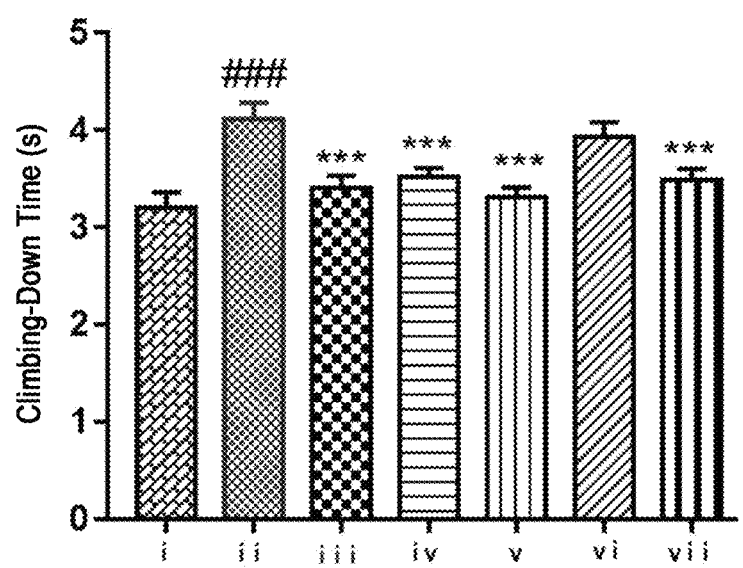
FIG. 11 shows the effects of different oligosaccharide compositions and the mannuronic diacid hexasaccharide on the climbing-down time of PD animals on day 11; wherein the symbols on the abscissa of the Figure are the same as those in FIG. 9.
Figure 12:
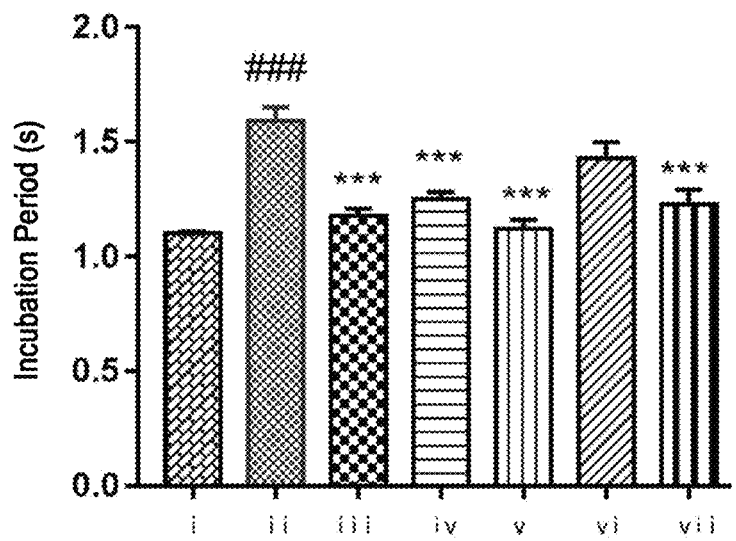
FIG. 12 shows the effects of different oligosaccharide compositions and the mannuronic diacid hexasaccharide on the incubation period of PD animals on day 11; wherein the symbols on the abscissa of the Figure are the same as those in FIG. 9.

In the test, compared with the blank control group, the incubation period and climbing-down time of the model group were significantly longer. Compared with the model group, the incubation period and climbing-down time of each dosing group were shortened to varying degrees. Among them, the pharmacodynamic activities of products A, B, and C were better than that of the mannuronic diacid hexasaccharide with a single polymerization degree, which was previously expected to be the most active. But the activity of product D was weaker than that of the mannuronic diacid hexasaccharide. Without being bound by any theory, it is speculated that the content of guluronic acid in the composition and the proportions of dissacharide to hexasaccharide have a significant effect on the activity of the product, however, when the proportion of guluronic acid is too high, the activity of the composition would decrease. See FIGS. 11 and 12.

3. Evaluation of Anti-Inflammatory-Reaction Pharmacodynamic Evaluation (1) Collagen-Induced Arthritis Mouse Model In the test, compared with the normal control group, the model group showed obvious symptoms of arthritis, and moderate erythema and swelling of ankle joints, wrist joints and metatarsal bones. The clinical score reached 6 points, indicating that the arthritis model was successfully established. Compared with the model group, the morbidity of each dosing group was reduced to different degrees. Products A, B, and C significantly delayed the onset time of the mice compared with the mannuronic diacid hexasaccharide with a single polymerization degree, and the clinical score was also lower compared with the mannuronic diacid hexasaccharide, indicating that the pharmacodynamic activities of products A, B, and C were better than the pharmacodynamic activity of the mannuronic diacid hexasaccharide. But the onset of product D was earlier and the clinical score was higher, reflecting that the activity of product D was weaker than the mannuronic diacid hexasaccharide. It demonstrates that the content of the guluronic acid and the proportion of disaccharide to hexasaccharide in the composition have significant effects on the product's activity. However, when the content of the guluronic acid is too high, the activity of the composition would decrease.

(2) MOG-Induced Multiple Sclerosis Mouse Model

In the experiment, compared with the normal control group, most mice in the model group showed weakness and paralysis in both hind limbs. The average clinical score of the model group reached 3 points, indicating that the multiple sclerosis model was successfully established. Compared with the model group, the inflammation progression of each dosing group was reduced to varying degrees. The clinical scores of products A, B, and C during the entire experiment and at the end point were lower than the mannuronic diacid hexasaccharide, indicating the pharmacodynamic activities of products A, B, and C were better than that of mannuronic diacid hexasaccharide; while the clinical score of product D during the entire experiment and at the end point were slightly higher, indicating the anti-inflammatory activity of product D was the weakest. It demonstrates that the content of the guluronic acid and the proportion of disaccharide to hexasaccharide in the composition have significant effects on the product's activity. However, when the content of the guluronic acid is too high, the activity of the composition would decrease.

(3) MRL/Lpr Lupus Erythematosus Mouse Model

Starting from week 10, the transgenic mice began to develop disease and lymph node swelling occurred, and the lymph node score continued to increase over time, indicating that the model group had successfully developed the disease and the disease progressed rapidly. Compared with the model group, the disease progression of each dosing group was reduced to different degrees. Products A, B, and C significantly delayed the onset time of mice compared with the mannuronic diacid hexasaccharide, and the lymph node score was also lower than that of the mannuronic diacid hexasaccharide, indicating the pharmacodynamic activities of products A, B, and C were better than that of mannuronic diacid hexasaccharide. However, the onset time of product D was earlier and its lymph node score was higher, reflecting that the activity of product D was weaker than that of the mannuronic diacid hexasaccharide. It demonstrates that the content of the guluronic acid and the proportion of disaccharide to hexasaccharide in the composition have significant effects on the product's activity. However, when the content of the guluronic acid is too high, the activity of the composition would decrease.

(4) Dextran Sulfate Sodium (DSS)-Induced Colitis Mouse Model

Figure 13A:
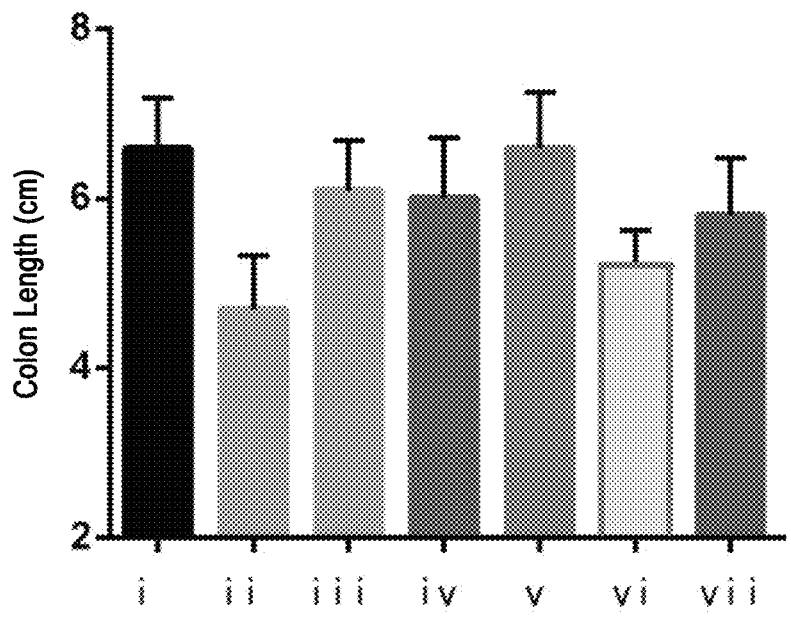
FIGS. 13*a* and 13*b* show the therapeutic effects of different oligosaccharide compositions and the mannuronic diacid hexasaccharide on inflammatory enteritis in mice; the symbols on the abscissa of the Figure are the same as those in FIG. 9.
Figure 13B:
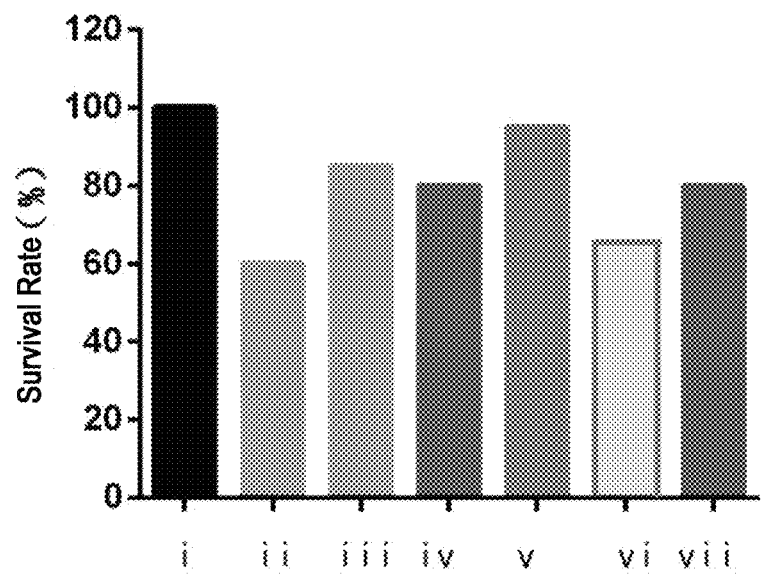

After the completion of the test, compared with the normal control group, the colon in the model group was significantly shortened due to inflammation, and most of the mice lost weight. Nearly half of the animals in the model group died later, indicating that the intestinal inflammation was very serious. Compared with the model group, the intestinal inflammation of each dosing group was reduced to varying degrees, which was reflected in the recovery of colon length and improved survival rate. From FIGS. 13a and 13b, it could be seen that products A, B, and C made the mouse colon length and animal survival rate greater than those of the mannuronic diacid hexasaccharide, indicating that the pharmalogical activities of products A, B, and C were all better than the pharmalogical activity of the mannuronic diacid hexasaccharide. However, product D had a smaller colon length and a slightly lower survival rate compared with the mannuronic diacid hexasaccharide, reflecting that the activity of product D was weaker than that of the mannuronic diacid hexasaccharide. Similarly, the test results were consistent with the previous tests, indicating that the content of the guluronic acid and the proportion of disaccharide to hexasaccharide in the composition have significant effects on the product's activity. However, when the content of the guluronic acid is too high, the activity of the composition would decrease.

4. Evaluation of Anti-Diabetes Mellitus Pharmacodynamic Evaluation

Figure 14:
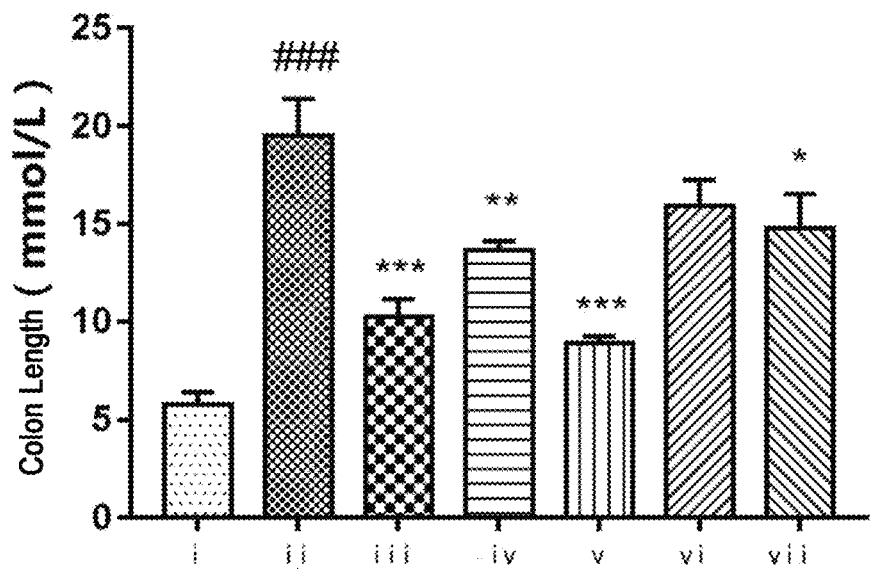
FIG. 14 shows the effects of different oligosaccharide compositions and the mannuronic diacid hexasaccharide on postprandial blood glucose in diabetic mice; the symbols on the abscissa of the Figure are the same as those in FIG. 9.

In the test, the model group was compared with the normal control group, and the postprandial blood glucose of the model group was significantly higher, indicating that the evaluation model was successfully established. Compared with the model group, the postprandial blood glucose of each dosing group was significantly lower. Among them, the pharmacodynamic activities of products A, B, and C were better than the pharmacodynamic activity of the mannuronic diacid hexasaccharide, but the activity of product D was weaker than that of the mannuronic diacid hexasaccharide. The test results were consistent with the previous tests, indicating that the content of the guluronic acid and the proportion of disaccharide to hexasaccharide in the composition have significant effects on the product's activity. However, when the content of the guluronic acid is too high, the activity of the composition would decrease. See FIG. 14.

Figure 15:
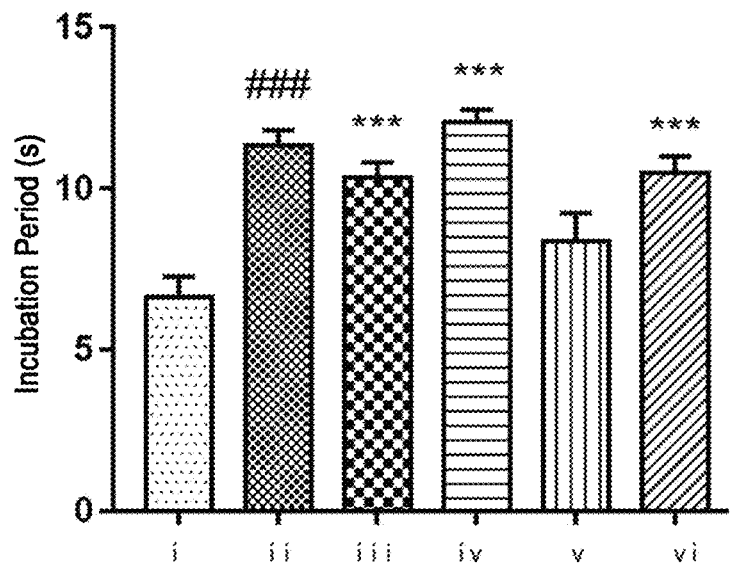
FIG. 15 shows the effects of different oligosaccharide compositions and the mannuronic diacid hexasaccharide on the incubation period of writhing response in mice induced by acetic acid; the samples corresponding to the numbers on the abscissa in the Figure are the following: i: model group; ii: product A; iii: product B; iv: product C; v: product D; vi: the mannuronic diacid hexasaccharide.
Figure 16:
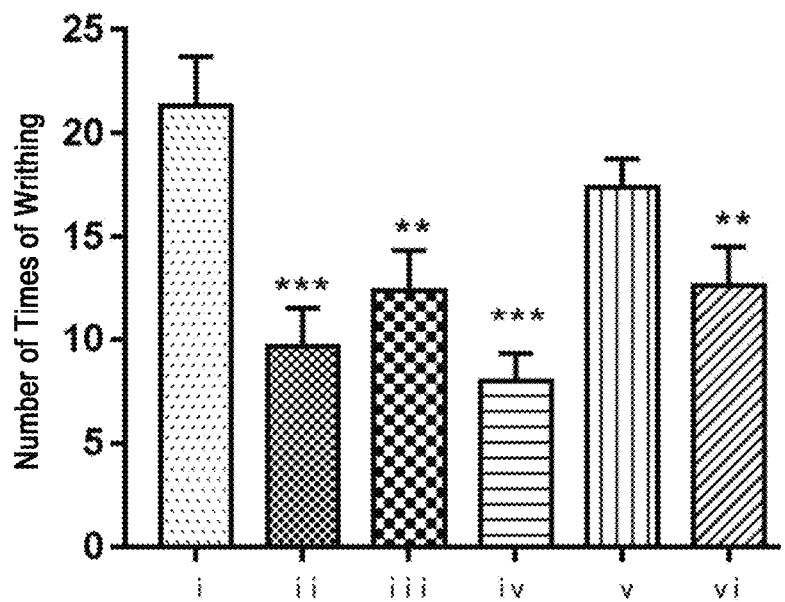
FIG. 16 shows the effects of different oligosaccharide compositions and the mannuronic diacid hexasaccharide on number of times of writhing response in mice induced by acetic acid; wherein the symbols on the abscissa of the Figure are the same as those in FIG. 15.

5. Evaluation of Anti-Pain Pharmacodynamic Evaluation (1) A Mouse Pain Model Induced by Acetic Acid In the test, compared with the blank control group, the incubation period of writhing of the model group was significantly shorter and the number of times of writhing was significantly increased, indicating that the evaluation model was successfully established. Compared with the model group, the incubation period of writhing of each dosing group was significantly prolonged, and the number of times of writhing was significantly reduced. Among them, products A, B, and C enabled the incubation period of writhing in mice to be longer than that of the mannuronic diacid hexasaccharide, and enabled the number of times of writhing to be smaller than that of the mannuronic diacid hexasaccharide, indicating the pharmacodynamic activities of products A, B, and C were better than that of the mannuronic diacid hexasaccharide. However, product D had a shorter incubation period of writhing and a slightly larger number of times of writhing compared with the mannuronic diacid hexasaccharide, reflecting that the activity of product D was weaker than that of the mannuronic diacid hexasaccharide. Similarly, the test results were consistent with the previous tests, indicating that the content of the guluronic acid and the proportion of disaccharide to hexasaccharide in the composition have significant effects on the product's activity. However, when the content of the guluronic acid is too high, the activity of the composition would decrease. See FIGS. 15 and 16.

(2) A Migraine Rat Model Induced by Nitroglycerin

Figure 17:
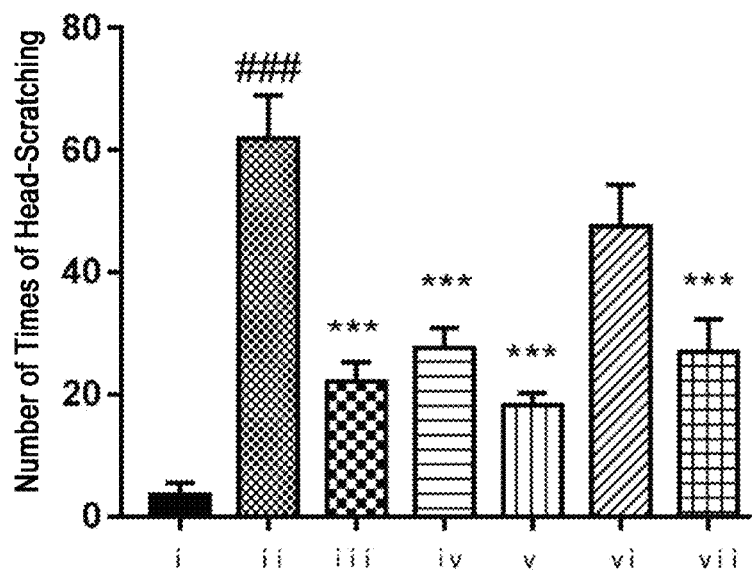
FIG. 17 shows the effects of different oligosaccharide compositions and the mannuronic diacid hexasaccharide on the number of times of head scratching in migraine rats induced by nitroglycerin; wherein the symbols on the abscissa of the Figure are the same as those in FIG. 9.

The rats developed ear redness about 3 minutes after subcutaneous injection of nitroglycerin, which lasted for about 2.5 hours. The number of times of head scratching within the 30-45 minutes after modeling in the model group was significantly more than that of the blank control group. Compared with the model group, the dosing group showed a significant delay in the appearance of the ear redness, shortened duration time of the ear redness, and decreased number of times of head scratching within the 30-45 minute period. Among them, products A, B, and C enabled the number of times of head scratching in rat to be less than that of the mannuronic diacid hexasaccharide, indicating that pharmalogical activities of products A, B, C, and D were all better than the pharmalogical activity of the mannuronic diacid hexasaccharide. However, product D had a slightly larger number of times of head scratching in mice compared with the mannuronic diacid hexasaccharide, reflecting that the activity of product D was weaker than that of the mannuronic diacid hexasaccharide. Similarly, the test results were consistent with the previous tests, indicating that the content of the guluronic acid and the proportion of disaccharide to hexasaccharide in the composition have significant effects on the product's activity. However, when the content of the guluronic acid is too high, the activity of the composition would decrease. See FIG. 17.

Figure 18:
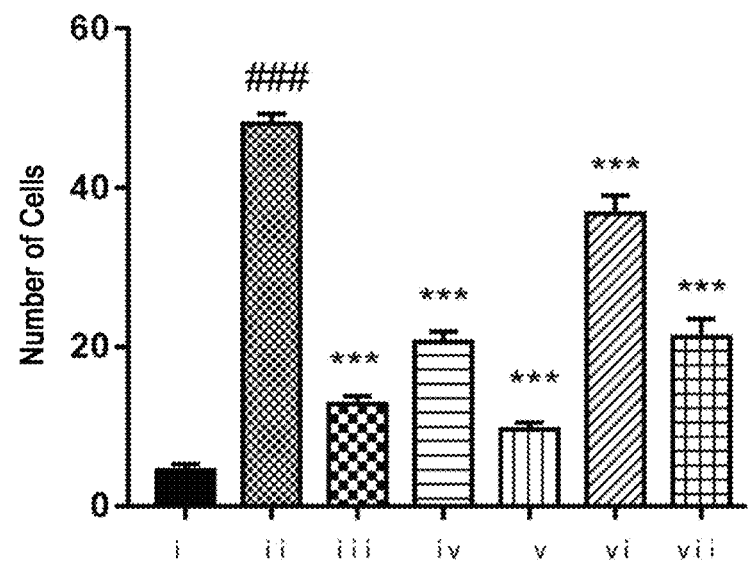
FIG. 18 shows the effects of different oligosaccharide compositions and the mannuronic diacid hexasaccharide on the number of c-fos positive cells in caudal part (nucleus caudalis) of the spinal trigeminal nucleus in migraine rats induced by electrical stimulation of the trigeminal ganglion; wherein the symbols on the abscissa of the Figure are the same as those in FIG. 9.

(3) A Migraine Model Induced by Electrical Stimulation of the Trigeminal Ganglion Electrical stimulation of the rat trigeminal ganglion obviously caused dural serum protein exudation. Compared with the blank control group and the sham operation group, the PPE rate was significantly increased, and the number of c-fos expression positive cells was significantly increased in the model group. Compared with the model group, the PPE rate was significantly reduced and the number of c-fos expression positive cells was significantly reduced in the dosing group. Among them, the numbers of c-fos expression positive cells in products A, B, and C were less than that in the mannuronic diacid hexasaccharide, indicating that pharmalogical activities of products A, B, C, and D were all better than the pharmalogical activity of the mannuronic diacid hexasaccharide. However, product D had a slightly larger number of c-fos expression positive cells compared with the mannuronic diacid hexasaccharide, reflecting that the activity of product D was weaker than that of the mannuronic diacid hexasaccharide. Similarly, the test results were consistent with the previous tests, indicating that the content of the guluronic acid and the proportion of disaccharide to hexasaccharide in the composition have significant effects on the product's activity. However, when the content of the guluronic acid is too high, the activity of the composition would decrease. See FIG. 18.

6. Evaluation of Anti-Vascular Dementia Pharmacodynamic Evaluation (1) A Mouse Model with Vascular Dementia Caused by Bilateral Common Carotid Artery Occlusion (BCCAo)

1.1 Test Results of the Darkness Avoidance Test

Figure 19:
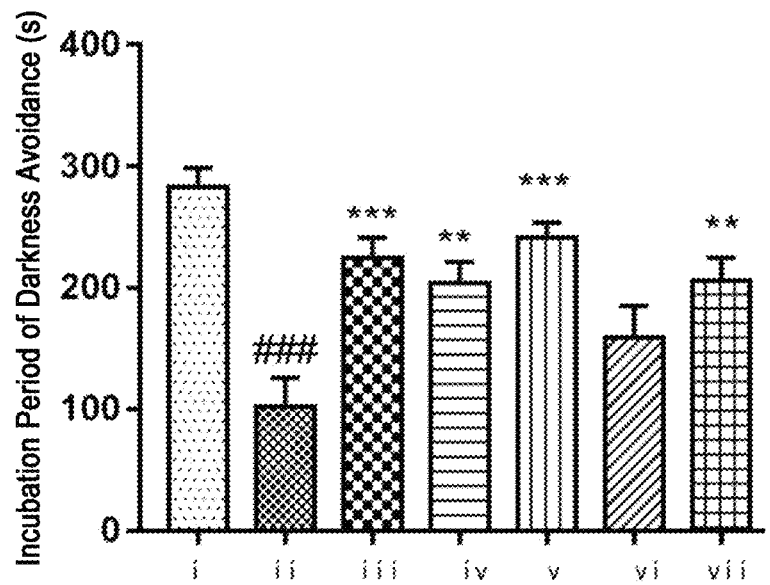
FIG. 19 shows the effects of different oligosaccharide compositions and the mannuronic diacid hexasaccharide on the incubation period in the darkness avoidance test in mice with vascular dementia caused by bilateral common carotid artery occlusion; wherein the symbols on the abscissa of the Figure are the same as those in FIG. 9.
Figure 20:
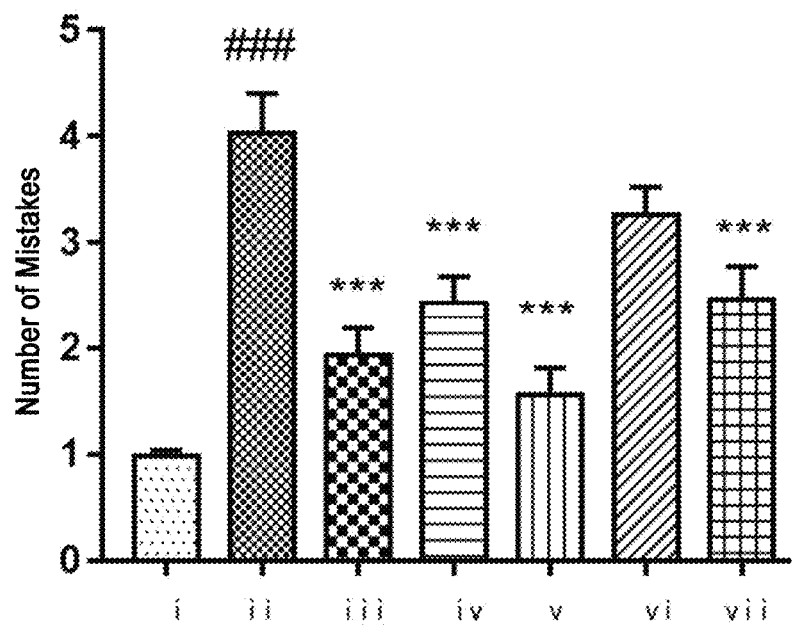
FIG. 20 shows the effects of different oligosaccharide compositions and the mannuronic diacid hexasaccharide on the number of mistakes in the darkness avoidance test in mice with vascular dementia caused by bilateral common carotid artery occlusion; wherein the symbols on the abscissa of the Figure are the same as those in FIG. 9.

In the test, the model group was compared with the sham operation control group. For the model group, the incubation period in the darkness avoidance test was significantly shorter, and the number of mistakes was significantly increased, indicating that the memory ability of the mice in the model group was significantly reduced, and the evaluation model was successfully established. Compared with the model group, the incubation period in the darkness avoidance test in each dosing group was significantly increased, and the number of mistakes was significantly reduced. Among them, the incubation periods of the mice in the groups of products A, B, and C were longer than that in the mannuronic diacid hexasaccharide, indicating that pharmalogical activities of products A, B, C, and D were all better than the pharmalogical activity of the mannuronic diacid hexasaccharide. However, product D had a slightly shorter incubation period of the mice compared with the mannuronic diacid hexasaccharide, reflecting that the activity of product D was weaker than that of the mannuronic diacid hexasaccharide. Similarly, the test results were consistent with the previous tests, indicating that the content of the guluronic acid and the proportion of disaccharide to hexasaccharide in the composition have significant effects on the product's activity. However, when the content of the guluronic acid is too high, the activity of the composition would decrease. See FIGS. 19 and 20.

1.2 Morris Water Maze Test Results

Figure 21:
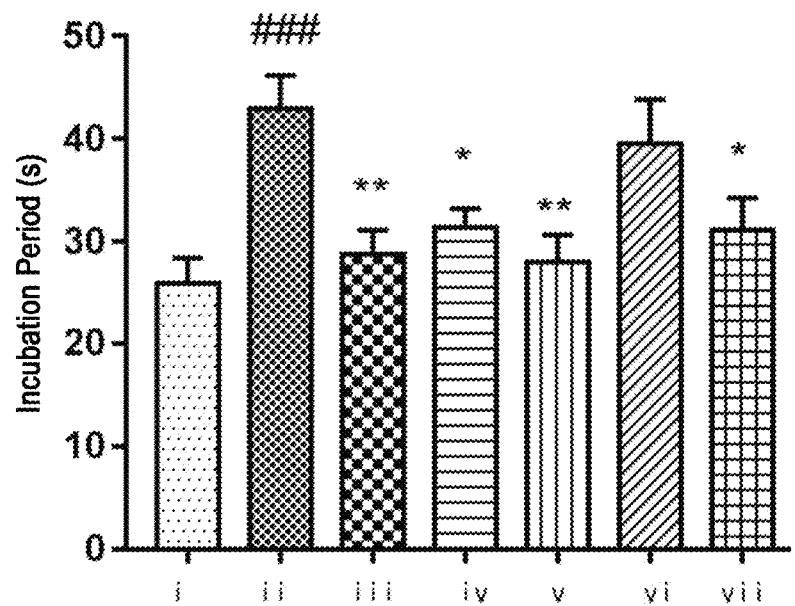
FIG. 21 shows the effects of different oligosaccharide compositions and the mannuronic diacid hexasaccharide on the escape incubation period in the water maze test in mice with vascular dementia caused by bilateral common carotid artery occlusion; wherein the symbols on the abscissa of the Figure are the same as those in FIG. 9.

In the test, compared with the sham operation group, the escape incubation period in the Morris water maze test of the mice in the model group was significantly longer, indicating that the BCCAo-induced vascular dementia mouse model was successfully established. Compared with the model group, the escape incubation period of each dosing group was significantly shorter. Among them, the escape incubation periods of the mice in the groups of products A, B, and C were shorter than that in the mannuronic diacid hexasaccharide, indicating that pharmalogical activities of products A, B, C, and D were all better than the pharmalogical activity of the mannuronic diacid hexasaccharide. However, product D had a slightly longer escape incubation period compared with the mannuronic diacid hexasaccharide, reflecting that the activity of product D was weaker than that of the mannuronic diacid hexasaccharide. See FIG. 21.

Figure 22:
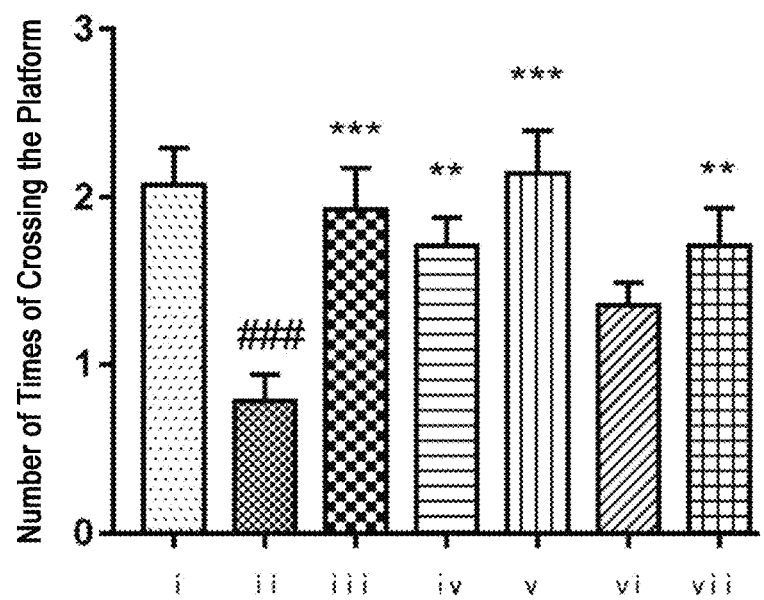
FIG. 22 shows the effects of different oligosaccharide compositions and the mannuronic diacid hexasaccharide on the number of times of crossing platform in mice with vascular dementia caused by bilateral common carotid artery occlusion; wherein the symbols on the abscissa of the Figure are the same as those in FIG. 9.
Figure 23:
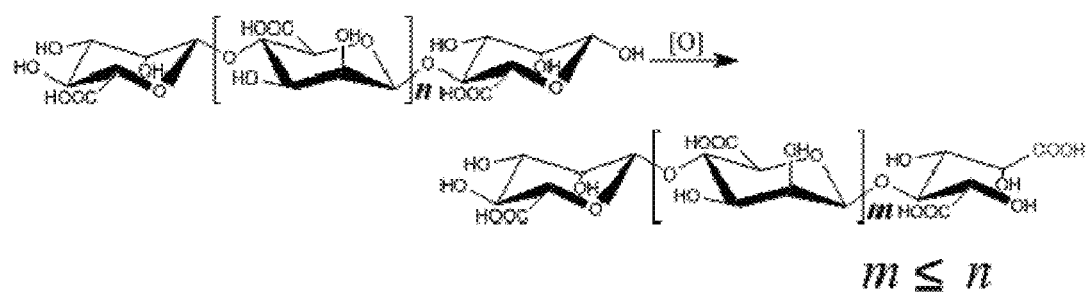
FIG. 23 shows reaction equation (V) to obtain mannuronic diacid as disclosed in prior documents.

Four days after the water maze place navigation test, the platform was removed. The spatial probe test was conducted to observe the number of times the animals crossed the platform. Compared with the sham operation group, the number of times that the mice crossed the original platform in the model group was significantly reduced, indicating that the memory ability of the BCCAo mice was significantly reduced; while the number of times the mice crossed the original platform in each dosing group was increased. Among them, the number of times the mice crossed the platform in the groups of products A, B, and C were higher than that in the mannuronic diacid hexasaccharide, indicating that pharmalogical activities of products A, B, C, and D were all better than the pharmalogical activity of the mannuronic diacid hexasaccharide. However, product D had a slightly lower number of times the mice crossed the platform compared with the mannuronic diacid hexasaccharide, reflecting that the activity of product D was weaker than that of the mannuronic diacid hexasaccharide. See FIG. 22.

(2) The Effect in the Rats with Vascular Dementia Caused by Middle Cerebral Artery Occlusion (MCAO)

In the test, compared with the sham operation group, the escape incubation period in the Morris water maze test of the rats in the model group was significantly longer, indicating that the MCAO-induced mouse vascular dementia model was successfully established. Compared with the model group, the escape incubation period of each dosing group was significantly shorter. Among them, the escape incubation periods of the rats in products A, B, and C were shorter than that in the mannuronic diacid hexasaccharide, indicating that pharmalogical activities of products A, B, C, and D were all better than the pharmalogical activity of the mannuronic diacid hexasaccharide. However, product D had a slightly longer escape incubation period compared with the mannuronic diacid hexasaccharide, reflecting that the activity of product D was weaker than that of the mannuronic diacid hexasaccharide.

One day after the place navigation test was finished, a spatial probe test was performed to observe and determine the number of times the animal crossed the platform within 2 minutes. Compared with the sham operation group, the number of times the rats crossed the original platform was significantly reduced in the model group, indicating that the memory ability of the rats in the MCAO group was significantly reduced; while the number of times the rats crossed the original platform in each dosing group was increased. Among them, the number of times the rats crossed the platform in products A, B, and C were higher than that in the mannuronic diacid hexasaccharide, indicating that pharmalogical activities of products A, B, C, and D were all better than the pharmalogical activity of the mannuronic diacid hexasaccharide. However, product D had a slightly lower number of times the rats crossed the platform compared with the mannuronic diacid hexasaccharide, reflecting that the activity of product D was weaker than that of the mannuronic diacid hexasaccharide.

The invention claimed is:

1. An alginic saccharic diacid composition comprising a mixture of mannuronic acid and guluronic acid of Formula (IV) or a pharmaceutically acceptable salt thereof:

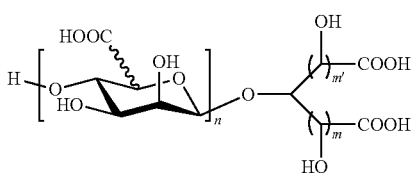

Formula (IV)

wherein
n is an integer selected from 1 to 9,
m is selected from 0, 1 or 2, m' is selected from 0 or 1, and wherein,
the total weight of alginic saccharic diacids wherein n=1-5 accounts for more than 60% of the total weight of the composition;
wherein, the total weight of guluronic acids accounts for 1%-30% of the total weight of the composition; and
wherein the total weight of the alginic saccharic diacids wherein m+m'=1 and 2 is no less than 50% of the total weight of the composition.

2. The alginic saccharic diacid composition of claim 1, wherein the total weight of the alginic saccharic diacids wherein m+m'=1 is no less than 10% of the total weight of the composition.

3. The alginic saccharic diacid composition of claim 1, wherein the total weight of the alginic saccharic diacids wherein m+m'=2 is no less than 10% of the total weight of the composition.

4. The alginic saccharic diacid composition of claim 1, wherein the total weight of the alginic saccharic diacids wherein n=1-5 accounts for 80%-95% of the total weight of the composition.

5. The alginic saccharic diacid composition of claim 1, wherein the total weight of the alginic saccharic diacids wherein n=1-3 accounts for 20%-70% of the total weight of the composition.

6. The alginic saccharic diacid composition of claim 1, wherein the ratio of the total weight of the alginic saccharic diacids wherein n=1-3 to the total weight of the alginic saccharic diacids wherein n=4-7 is between 1.0 and 3.5.

7. The alginic saccharic diacid composition of claim 6, wherein the ratio of the total weight of the alginic saccharic diacids wherein n=1-3 to the total weight of the alginic saccharic diacids wherein n=4-7 is between 1.0 and 3.0.

8. The alginic saccharic diacid composition of claim 1, wherein the weight percentage content of the alginic saccharic diacids with each of polymerization degrees in the composition is: n=1 5-25%, n=2: 15-30%, n=3: 15-28%, n=4: 10-25%, n=5: 5-15%, n=6: 3-10%, n=7: 2-5%, n=8: 1-5%, n=9: 1-5%.

9. The alginic saccharic diacid composition of claim 8, wherein the weight percentage content of the alginic saccharic diacids with each of polymerization degrees in the composition is: n=1 10-20%, n=2: 18-30%, n=3: 15-28%, n=4: 15-20%, n=5: 5-10%, n=6: 3-5%, n=7: 2-3%, n=8: 1-3%, n=9: 1-3%.

10. The alginic saccharic diacid composition of claim 1, wherein the pharmaceutically acceptable salt is sodium salt or potassium salt.

11. A pharmaceutical composition or health care product comprising an effective amount of the alginic saccharic diacid composition of claim 1 and a suitable carrier when necessary.

12. A method of treating a patient suffering from Alzheimer's disease, Parkinson's disease, inflammation, pain, Diabetes Mellitus or vascular dementia, comprising administering an effective amount of the alginic saccharic diacid composition of claim 1 to a patient in need thereof.

13. The alginic saccharic diacid composition of claim 1, wherein the total weight of the alginic saccharic diacids wherein m+m'=1 and 2 is 60%-90% of the total weight of the composition.

14. The alginic saccharic diacid composition of claim 1, wherein the total weight of the alginic saccharic diacids wherein m+m'=1 is 30%-40% of the total weight of the composition.

15. The alginic saccharic diacid composition of claim 1, wherein the total weight of the alginic saccharic diacids wherein m+m'=2 is 30%-50% of the total weight of the composition.

16. The alginic saccharic diacid composition of claim 9, wherein the pharmaceutically acceptable salt is sodium salt or potassium salt.

17. A pharmaceutical composition or health care product comprising an effective amount of the alginic saccharic diacid composition of claim 9 and a suitable carrier when necessary.

\* \* \* \* \*